(12) United States Patent
Matsuura et al.

(10) Patent No.: US 7,160,733 B2
(45) Date of Patent: Jan. 9, 2007

(54) LIGAND SPECIFIC TO $\beta_2$-GLYCOPROTEIN I AND USE THEREOF

(75) Inventors: Eiji Matsuura, 20-801, Nishinocho 7-chome, Okayama-shi, Okayama (JP); Kazuko Kobayashi, Okayama (JP)

(73) Assignee: Eiji Matsuura, Okayama (JP)

( * ) Notice: Subject to any disclaimer, the term of this patent is extended or adjusted under 35 U.S.C. 154(b) by 61 days.

(21) Appl. No.: 10/488,688

(22) PCT Filed: Jan. 30, 2002

(86) PCT No.: PCT/JP02/00723

§ 371 (c)(1),
(2), (4) Date: Jul. 12, 2004

(87) PCT Pub. No.: WO03/022866

PCT Pub. Date: Mar. 20, 2003

(65) Prior Publication Data

US 2004/0241858 A1     Dec. 2, 2004

(30) Foreign Application Priority Data

Sep. 7, 2001    (JP) .............................. 2001-272475

(51) Int. Cl.
*G01N 33/566*    (2006.01)
*G01N 33/543*    (2006.01)
*C07J 9/00*    (2006.01)
(52) U.S. Cl. ...................... 436/501; 435/7.5; 435/7.92; 435/975; 436/815; 552/551
(58) Field of Classification Search ................ 552/551; 435/7.5, 7.92, 975; 436/815, 501
See application file for complete search history.

(56) References Cited

U.S. PATENT DOCUMENTS 4,304,726 A * 12/1981 Arakawa et al. ............ 552/542

FOREIGN PATENT DOCUMENTS

| WO | 82/03175 | 9/1982 |
| WO | 95/09363 | 4/1995 |

OTHER PUBLICATIONS

A. Brown et al, CAPLUS abstract 1996: 154608 (1996).*
A. Brown et al, Journal of Lipid Researc, vol. 37(2), pp. 320-335 (1996).*
H. Kamido et al, CAPLUS abstract 1995: 827805 (1995).*
H. Kamido et al, Journal of Lipid Research, vol. 36(9), pp. 1876-1886 (1995).*
H, Kamido et al, CAPLUS abstract 1992: 506650 (1992).*
H. Kamido et al, FEBS Letters (1992), vol. 304(2-3), pp. 269-272.*
FEBS Lett., 1992, 304(2-3), pp. 269-272.
E. L. Chernolovskaya et al., "Affinity Modification of Human Chromatin with Reactive Derivatives of Oligonucleotides", FEBS Letters, 1992, vol. 303, Nos. 2-3, pp. 269-271.
M. Mushifiq et al., "Synthesis of Some 1,5-Benzothiazepine Derivatives of the Stigmastane Series", Journal of Chem. Research, Synop., 1992, vol. 5, pp. 168-169.
Shafiullah et al. "Reaction of 1-Thioglycerol with some 3-Substituted Cholest-5-en-7-ones", Acta Chimica Hungarica, 1990, vol. 127, No. 5, pp. 705-710.
M.S. Ahmad et al., "Oxidation of Steroidal Compounds with Manganese(III) Acetate in the Presence of Propionic Acid and Propionic Anhydribe", J. Chem. Res., Synop., 1986, vol. 10, pp. 384-385.
J. I. Teng et al., "Sterol Metabolism-XL VI. Synthesis of Oxidized Cholesterol Fatty Acyl Esters", Journal of Steroid Biochemistry, 1981, vol. 14, No. 6, pp. 569-573.
K. Kobayashi et al., "A Specific Ligand for $\beta_2$-glycoprotein I Mediates Autoantibody-Dependent Uptake of Oxidized Low Density Lipoprotein by Macrophages", Journal of Lipid Research, 2001, vol. 42, No. 5, pp. 697-709.
A. J. Brown et al., "Cholesterol and Oxysterol Metabolism and Subcellular Distribution in Macrophage Foam Cells: Accumulation of Oxidized Esters in Lysosomes", Journal of Lipid Research, 2000, vol. 41, No. 2, pp. 226-236.
Bioorg. Khim., 1997, vol. 23, No. 8, pp. 675-679.
A. J. Brown et al., "Free and Esterified Oxysterol: Formation During Copper-Oxidation of Low Density Lipoprotein and Uptake by Macrophages", Journal of Lipid Research, 1996, vol. 37, No. 2, pp. 320-325.
H. Kamido et al., "Lipid Ester-Bound Aldehydes among Copper-Catalyzed Peroxidation Products of Human Plasma Lipoproteins", Journal of Lipid Research, 1995, vol. 36, No. 9, pp. 1876-1886.
H. Kamdo et al., "Identification of Core Aldehydes among *in vitro* Peroxidation Products of Cholesteryl Esters", Lipids, 1993, vol. 28, No. 4, pp. 331-336.

* cited by examiner

*Primary Examiner*—Mary E. Ceperley
(74) *Attorney, Agent, or Firm*—Wenderoth, Lind & Ponack, L.L.P.

(57) ABSTRACT

The cholesterol derivative, represented by the following formula (1):

(1)

wherein R represents a C3–C23 saturated or unsaturated aliphatic hydrocarbon residue having an optional substituent, and, to the cholesterol backbone, —OH, —CHO, —COOH, —OOH, or an epoxy group may be added, specifically binds to $\beta_2$-glycoprotein. By use of the derivative, $\beta_2$-glycoprotein or a similar substance can be assayed in a very practical manner. Through the assay, a disease can be detected in a very practical manner.

4 Claims, 20 Drawing Sheets

FIG.2
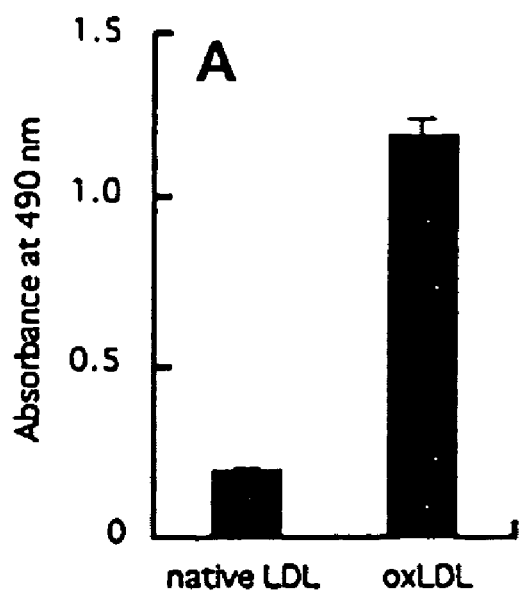
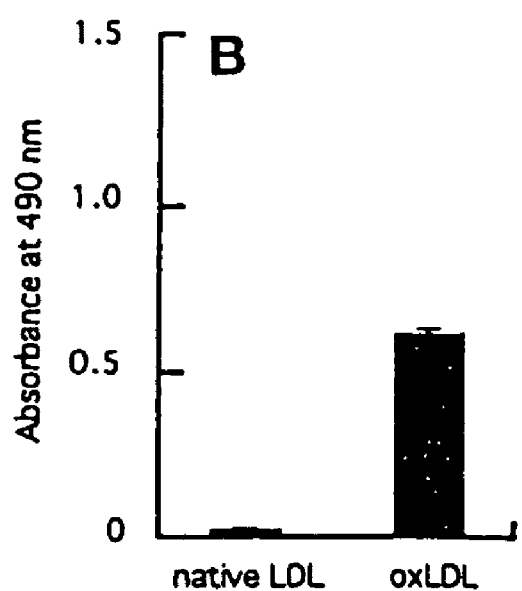
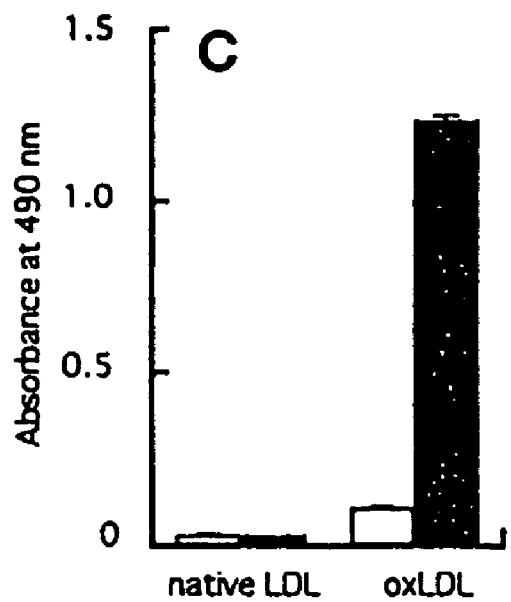
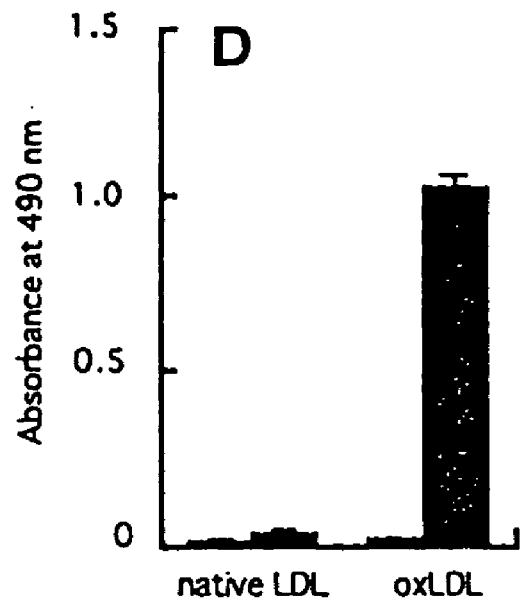

FIG. 11
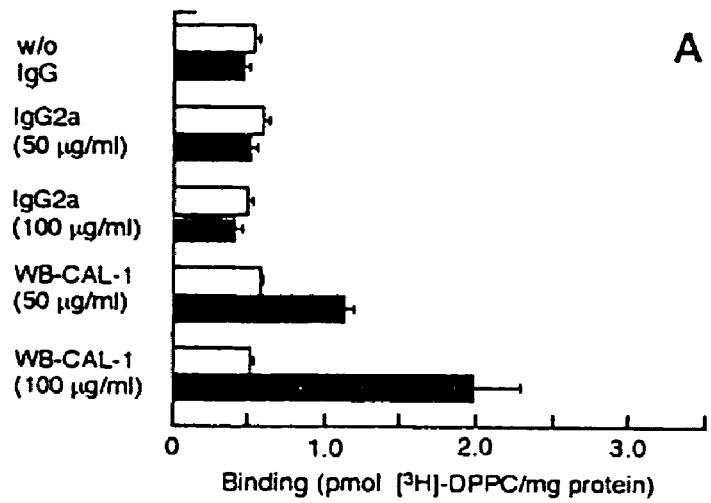
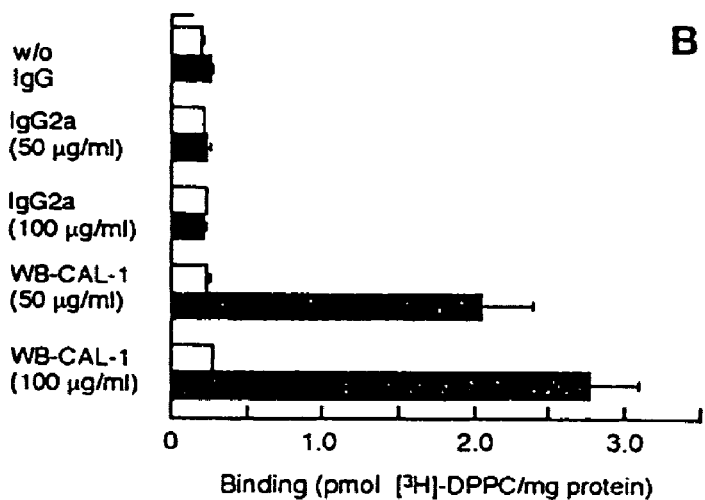
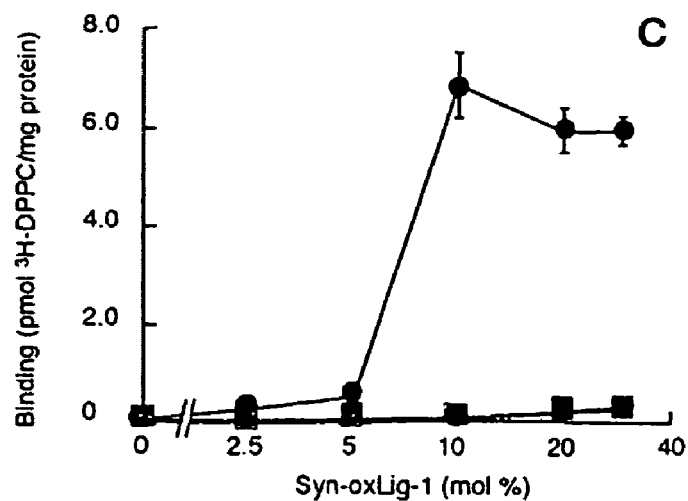

FIG.15
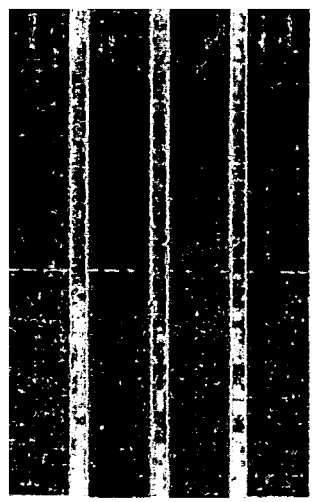
(A) I₂ vapor
(B) Cof-22
(C) EY2C9

FIG. 18
(A) cholesteryl linoleate:
5-cholesten-3β-ol 3-linoleate
FW 649, $C_{45}H_{76}O_2$
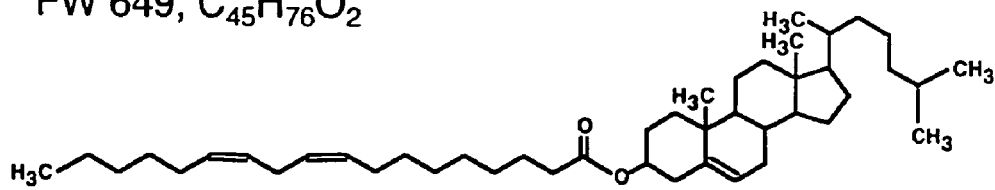
(B) oxLig-1:
9-oxo-9-(7-ketocholest-5-en-3β-yloxy)nonanoic acid
FW 570, $C_{36}H_{58}O_5$
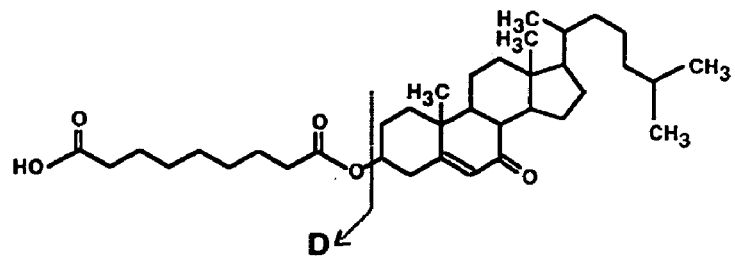
(C) oxLig-2:
4, 12-dioxo-12-(7-ketocholest-5-en-3β-yloxy)dodecanoic acid
FW 626, $C_{39}H_{62}O_6$
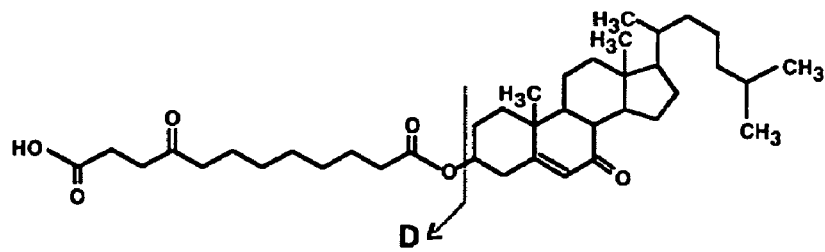
(D) 13-COOH-7KC:
13-oxo-13-(7-ketocholest-5-en-3β-yloxy)tridecanoic acid
FW 626, $C_{40}H_{66}O_5$
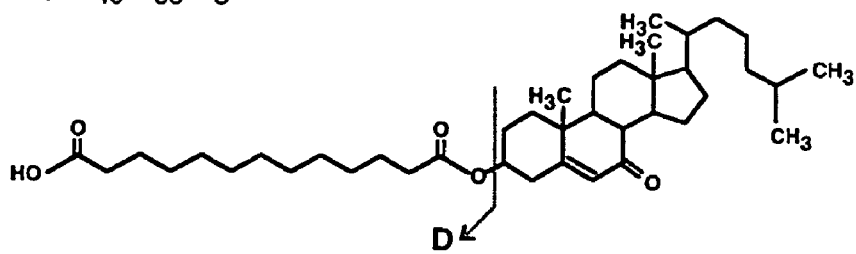

LIGAND SPECIFIC TO β₂-GLYCOPROTEIN I AND USE THEREOF

This application is a U.S. national stage of International Application No. PCT/JP02/00723 filed Jan. 30, 2002.

TECHNICAL FIELD

The present invention relates to a ligand specific to $\beta_2$-glycoprotein I ($\beta_2$-GPI) and derivatives of the ligand; to an assay method for $\beta_2$-GPI making use of any of the ligand and derivatives; to an assay method for an antibody recognizing a ligand-$\beta_2$-GPI complex; and to a method for detecting a disease.

BACKGROUND ART $\beta_2$-GPI is a major antigen which is present in patients with antiphospholipid syndrome (APS) and is recognized by "an antiphospholipid antibodies." $\beta_2$-GPI is known to specifically bind to oxidized low-density lipoprotein (oxidized LDL; oxLDL), but not to non-oxidized (native) low-density lipoprotein (LDL). PCT International Patent Publication (pamphlet) WO 95/9363 discloses an oxLDL assay method based on a specific binding property with respect to $\beta_2$-GPI, a kit for diagnosing an arteriosclerotic disease employing the assay method, etc.

However, the portion of the oxLDL structure which $\beta_2$-GPI recognizes for binding has not been identified.

Therefore, identification of the portion of the oxLDL structure to which $\beta_2$-GPI specifically binds would realize an assay of $\beta_2$-GPI or a similar assay by use of an easier and simpler system employing a substance including the portion. In addition, handling and storage of the reagents used in the assay would be further facilitated, leading to provision of constant-quality assay reagents, assay kits, etc. at low cost.

In view of the foregoing, the present inventors have carried out extensive studies in order to provide a substance having a structure which specifically binds to $\beta_2$-GPI; a very practical assay method for $\beta_2$-GPI or the like making use of the substance; and a very practical method for detecting a disease on the basis of the assay method. The inventors have isolated a substance having a structure which specifically binds to $\beta_2$-GPI, and based on the isolated substance, have established an assay method for $\beta_2$-GPI or the like as well as a method for detecting a disease employing the assay method. The present invention has been accomplished on the basis of these findings.

DISCLOSURE OF THE INVENTION

Accordingly, the present invention is directed to a cholesterol derivative represented by the following formula (1) (hereinafter referred to as the derivative of the present invention):

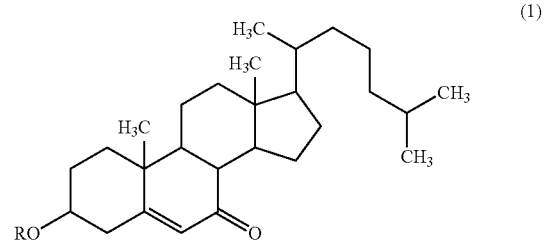

(1)

wherein R represents a C3–C23 saturated or unsaturated aliphatic hydrocarbon residue having an optional substituent, and, to the cholesterol backbone, —OH, —CHO, —COOH, —OOH, or an epoxy group may be added.

The aforementioned R preferably has one or more substituents selected from the group consisting of —COOH, —OH, —CHO, an oxo group, and an epoxy group.

R is preferably a C3–C23 saturated or unsaturated fatty acid residue which may have one or more oxo groups. More preferably, R is a group represented by HOOC—R'— (wherein R' represents a C2–C22 saturated or unsaturated aliphatic hydrocarbon residue which may have one or more oxo groups).

R' is preferably a linear-chain aliphatic hydrocarbon residue having one oxo group.

In relation to specific examples of the derivative of the present invention, the invention is also directed to cholesterol derivatives represented by the following formulas (2) to (7).

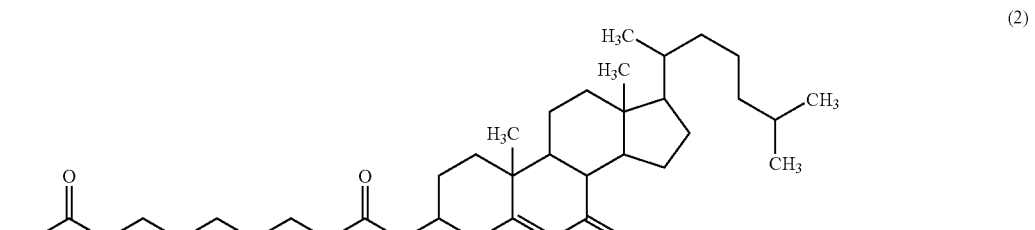

(2)

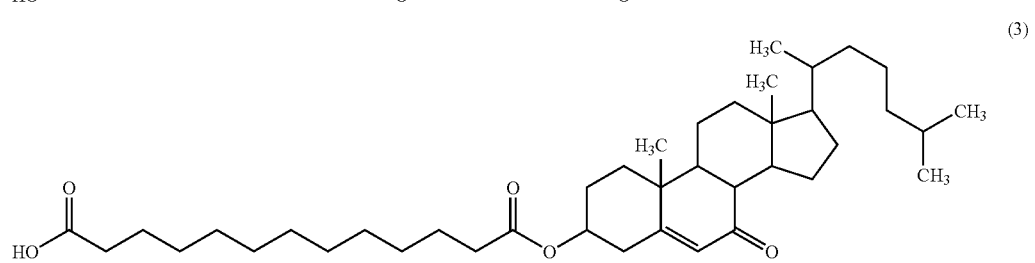

(3)

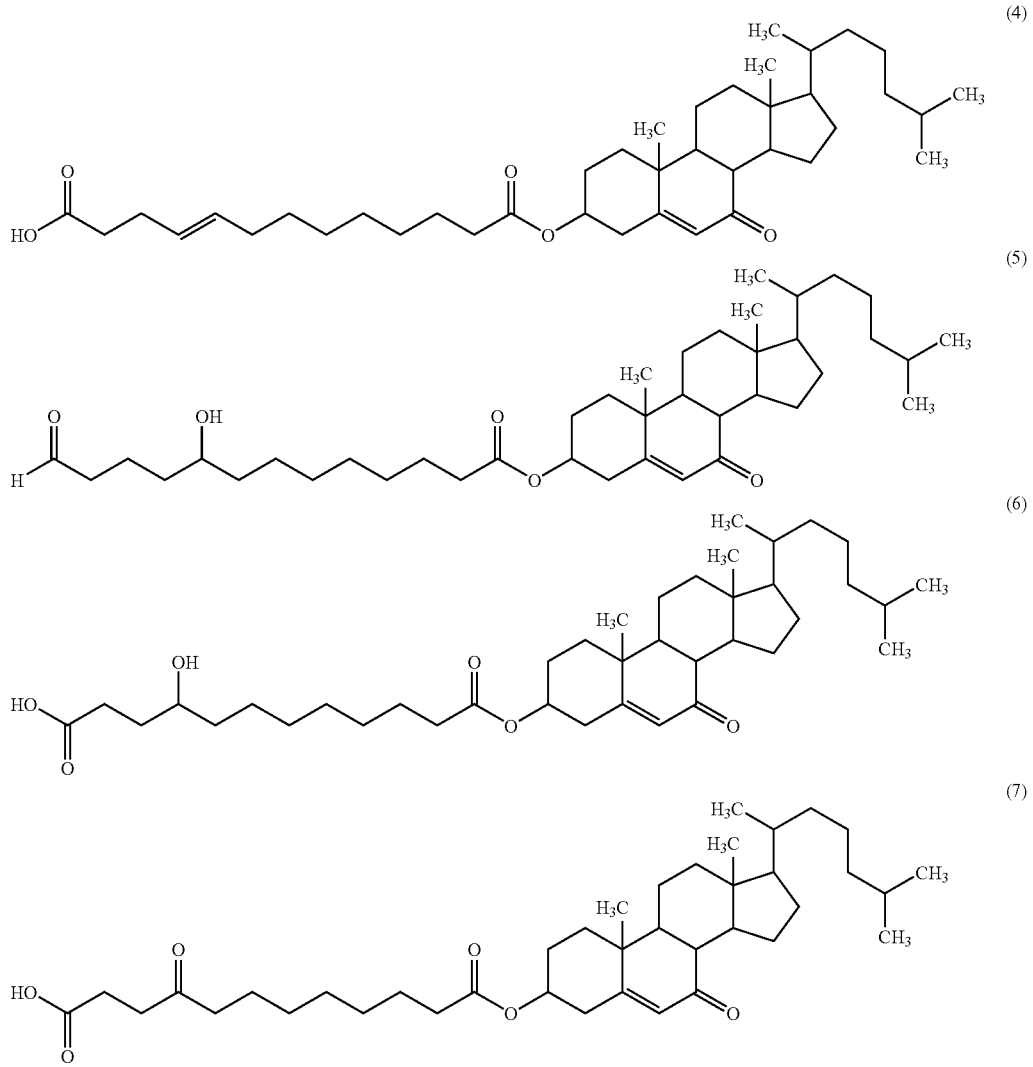

The present invention is also directed to a solid phase on which the derivative of the present invention has been immobilized (hereinafter referred to as the "solid phase of the present invention").

The present invention is also directed to an assay method for β$_2$-GPI, characterized in that the method includes at least the following steps (hereinafter referred to as "assay method 1 of the present invention"):

a step of forming a complex of β$_2$-GPI and the cholesterol derivative immobilized on the solid phase of the present invention by bringing a specimen into contact with the solid phase (Step 1); and a step of detecting β$_2$-GPI contained in the complex which has been formed in Step 1 (Step 2).

The present invention is also directed to an assay method for an antibody recognizing a "complex of β$_2$-GPI and the derivative of the present invention," characterized in that the method includes at least the following steps (hereinafter referred to as "assay method 2 of the present invention"):

a step of forming a complex of the "complex of β-GPI and the cholesterol derivative immobilized on the solid phase of the present invention" (hereinafter, the complex of β-GPI and the cholesterol derivative immobilized on the solid phase of the present invention is referred to as the "β$_2$-GPI-cholesterol derivative complex") and an antibody recognizing the β$_2$-GPI-cholesterol derivative complex by bringing β$_2$-GPI and a specimen into contact with the solid phase (Step 1); and a step of detecting the antibody contained in the complex which has been formed in Step 1 (Step 2).

The present invention is also directed to a method for detecting a disease (hereinafter referred to as the "detection method of the present invention"), characterized in that the method includes assaying an antibody recognizing the "complex of β$_2$-GPI and the derivative of the present invention" present in blood through the assay method 2 of the present invention and correlating the amount of the antibody present in blood to the disease. The disease is preferably an antiphospholipid syndrome or thrombosis. The thrombosis is preferably arterial thrombosis.

The present invention is also directed to an assay kit for β$_2$-GPI, characterized in that the kit comprises at least the following (A) and (B) (hereinafter referred to as assay kit 1 of the present invention):

the solid phase of the present invention (A) and a substance binding to $\beta_2$-GPI (B).

The present invention is also directed to an assay kit for an antibody recognizing "the complex of $\beta_2$-GPI and the derivative of the present invention," characterized in that the kit comprises at least the following (A) and (B) (hereinafter referred to as assay kit 2 of the present invention):

the solid phase of the present invention (A) and a substance binding to an antibody recognizing "the complex of $\beta_2$-GPI and the derivative of the present invention" (B).

The assay kit 2 of the present invention is preferably a kit for detecting a disease. The disease is preferably an antiphospholipid syndrome or thrombosis. The thrombosis is preferably arterial thrombosis.

The present invention will next be described in detail. First, abbreviations used in the specification are listed below.

aPL: Antiphospholipid antibody
aCL: Anticardiolipin antibody
APS: Antiphospholipid syndrome
$\beta_2$-GPI: $\beta_2$-Glycoprotein I
CL: Cardiolipin
LDL: Low-density lipoprotein
oxLDL: Oxidized LDL
$Cu^{2+}$-oxLDL: oxLDL formed through oxidation by $CuSO_4$
oxLig-1: Compound represented by formula (2), 9-oxo-9-(7-ketocholest-5-en-3$\beta$-yloxy)nonanoic acid, also called (7-ketocholesteryl-9-carboxynonanoate)
oxLig-2: Compound represented by formula (7), 4,12-dioxo-12-(7-ketocholest-5-en-3$\beta$-yloxy)dodecanoic acid
13-COOH-7KC: Compound represented by formula (3), 13-oxo-13-(7-ketocholest-5-en-3$\beta$-yloxy)tridecanoic acid
PS: Phosphatidylserine
SLE: Systemic lupus erythematosus
TLC: Thin-layer chromatography
HPLC: High-performance liquid chromatography
Chol: Cholesterol
DOPC: Dioleoylphosphatidylcholine
[$^3$H]DPPC: L-3-phosphatidyl[N-methyl-$^3$H]choline, 1,2-dipalmitoyl
DPPS: Dipalmitoylphosphatidylserine
PAPC: 1-Palmitoyl-2-arachidonoyl-phosphatidylcholine In the present specification, numerals enclosed by "[ ]" refer in principle to mentioned document Nos. of the below-mentioned references.

<1> Derivative of the Present Invention

The derivative of the present invention is a cholesterol derivative represented by the following formula (1):

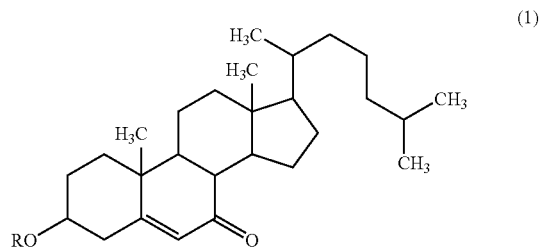

wherein R represents a C3–C23 saturated or unsaturated aliphatic hydrocarbon residue having an optional substituent. Among the hydrocarbon residues, a C5–C20 hydrocarbon residue is preferred, a C8–C15 residue is more preferred, and a C9–C13 residue is particularly preferred. To the cholesterol backbone, —OH, —CHO, —COOH, —OOH, or an epoxy group may be added. The aforementioned R preferably has one or more substituents selected from the group consisting of —COOH, —OH, —CHO, an oxo group, and an epoxy group.

R is preferably a C3–C23 saturated or unsaturated fatty acid residue which may have one or more oxo groups. Among the fatty acid residues, a C5–C20 fatty acid residue is preferred, a C8–C15 residue is more preferred, and a C9–C13 residue is particularly preferred.

R is preferably a group represented by HOOC—R'— (wherein R' represents a C2–C22 saturated or unsaturated aliphatic hydrocarbon residue which may have one or more oxo groups). Among the groups represented by HOOC—R'—, a C4–C19 group is preferred, a C7–C14 group is more preferred, and a C8–C12 group is particularly preferred.

R' is preferably a linear-chain aliphatic hydrocarbon residue, with a linear-chain aliphatic hydrocarbon residue having one oxo group being more preferred. The preferred number of carbon atoms of the aliphatic hydrocarbon residue is the same as described above.

Specific examples of the derivative of the present invention include the cholesterol derivatives represented by the following formulas (2) to (7), respectively.

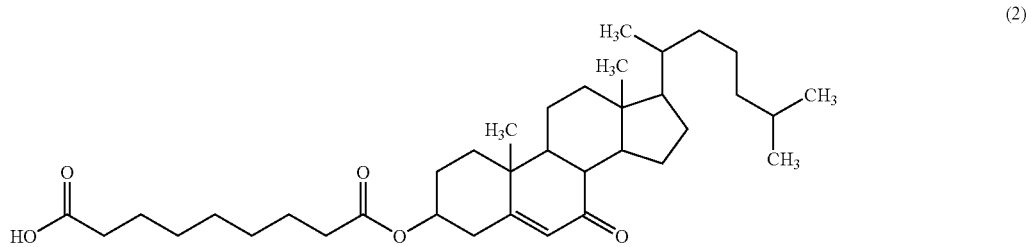

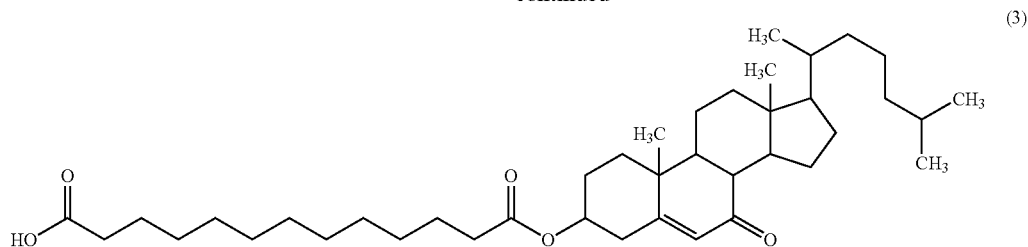
(3)
In the present specification, the substance represented by formula (3) is referred to as "13-COOH-7KC."
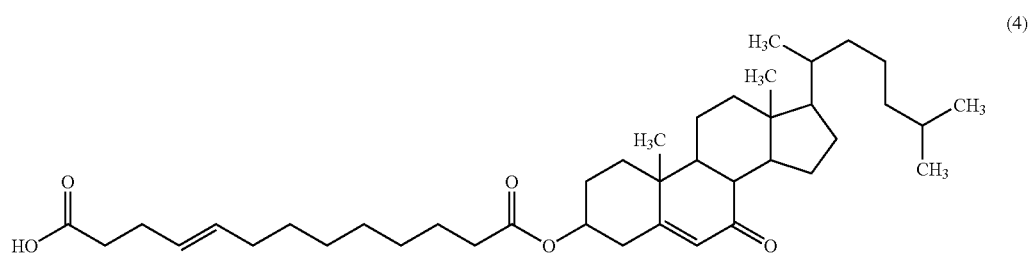
(4)
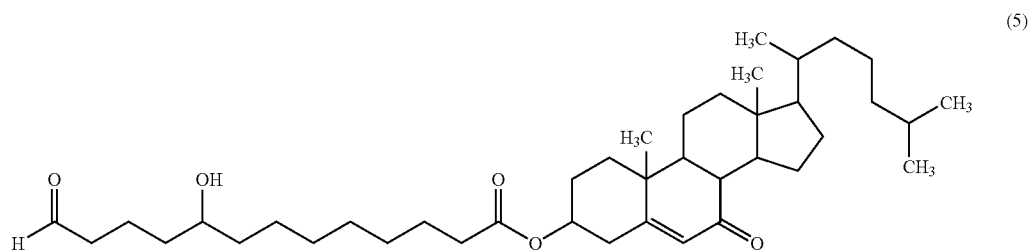
(5)
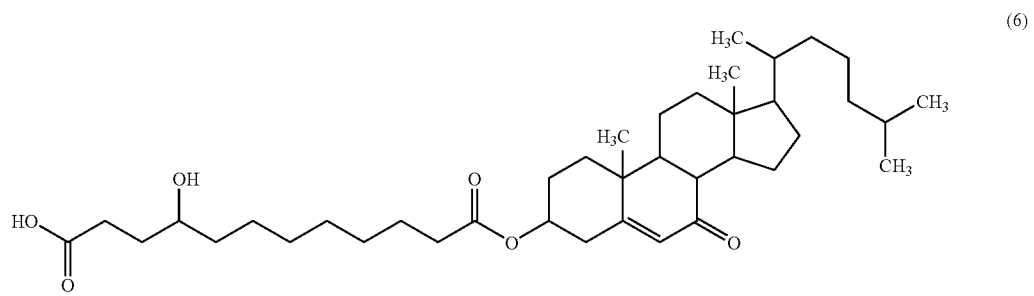
(6)
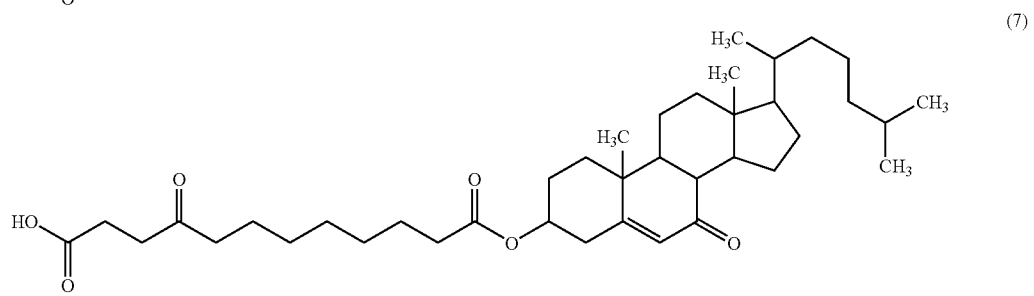
(7)

In the present specification, the substance represented by formula (7) is referred to as "oxLig-2."

The derivative of the present invention can be produced by isolating the same from oxLDL through the method described in the below-mentioned example. Alternatively, the derivative can be chemically synthesized through the method described in the below-mentioned example.

The synthesized or isolated derivative of the present invention can be identified through analyses such as NMR ($^1$H-NMR, $^{13}$C-NMR) analysis, mass spectrometry, and analysis of binding performance to $\beta_2$-GPI.

<2> Solid Phase of the Present Invention

The solid phase of the present invention is a solid phase on which the derivative of the present invention has been immobilized.

No particular limitation is imposed on the solid phase employed for immobilization of the derivative of the present invention thereon, so long as the solid phase can immobilize the derivative of the present invention thereon and is insoluble in water, a specimen, and a reaction mixture to be assayed. Examples of the form of the solid phase include plates (e.g., wells of a microplate), tube, beads, membrane, and gel. Examples of the solid phase material include polystyrene, polypropylene, nylon, and polyacrylamide.

Of these, a plate made of polystyrene is preferred.

In order to immobilize the derivative of the present invention onto the solid phase, a general immobilization method for lipid; e.g., the physical adsorption method or the covalent bond method, can be employed.

Of these, the physical adsorption method is preferred, since the method can be carried out in a simple manner and is often employed in the field.

In one specific mode of the physical adsorption method, the derivative of the present invention is dissolved in a solvent, such as ethanol, methanol, or a mixture of methanol and chloroform; the solution is brought into contact with the solid phase (e.g., a microplate); and the solvent is evaporated, thereby adsorbing the derivative of the present invention on the solid phase.

The surface of the solid phase on which the derivative of the present invention has been immobilized may include a surface portion on which the derivative has not yet been immobilized. If $\beta_2$-GPI or another molecular species contained in a specimen is attached on such a surface portion, accurate assay results may fail to be obtained. Thus, the portion on which the derivative of the present invention has not been immobilized is preferably covered with a blocking substance added prior to contact between a specimen and the solid phase. Examples of the blocking substance include serum albumin, casein, skim milk, and gelatin, and commercial blocking substance products can also be used.

In one specific blocking method, a blocking substance (e.g., serum albumin, casein, skim milk, or gelatin) is added to the solid phase, and the solid phase is stored at about 37° C. for 30 minutes to 2 hours or at ambient temperature (15 to 25° C.) for 1 to 2 hours.

<3> Assay Method of the Present Invention

The assay method 1 of the present invention is an assay method for $\beta_2$-GPI, characterized in that the method includes at least the following steps:

a step of forming a complex of $\beta_2$-GPI and the cholesterol derivative immobilized on the solid phase of the present invention by bringing a specimen into contact with the solid phase (Step 1); and a step of detecting $\beta_2$-GPI contained in the complex which has been formed in Step 1 (Step 2).

The steps will be described individually.

Step 1:

The description set forth regarding the solid phase of the present invention is also applicable herein.

No particular limitation is imposed on the specimen which is to be brought into contact with the solid phase of the present invention, so long as the specimen contains or may contain $\beta_2$-GPI, which is an assay target. Purification of the specimen in terms of $\beta_2$-GPI is optional, and may not be performed. Specific examples of the specimen include blood, serum, and plasma. No particular limitation is imposed on the method of bringing the specimen into contact with the solid phase of the present invention, so long as the molecules of the derivative of the present invention immobilized on the solid phase are brought into contact with the $\beta_2$-GPI molecules contained in the specimen. Specifically, the specimen may be added to the solid phase of the present invention so as to attain contact therebetween, or the solid phase of the present invention may be added to the specimen so as to attain contact therebetween.

After contact between the specimen and the solid phase has been attained, the system is preferably allowed to react for about one hour at, for example, 0 to 45° C., preferably 4 to 37° C., so as to sufficiently bind $\beta_2$-GPI contained in the specimen to the derivative of the present invention immobilized on the solid phase. After completion of reaction, preferably, the solid phase and the liquid phase are sufficiently separated from each other. Alternatively, washing of the solid phase is preferably carried out. For example, the surface of the solid phase is washed with a wash liquid, thereby removing non-specific adsorbed matter and non-reacted components present in the specimen.

Preferred examples of the wash liquid include buffers (e.g., phosphate buffer, PBS, and Tris-HCl buffer) to which a non-ionic surfactant such as a Tween series surfactant has been added.

Through contact between the specimen and the solid phase of the present invention, $\beta_2$-GPI contained in the specimen and the derivative of the present invention immobilized on the solid phase form a complex, whereby $\beta_2$-GPI contained in the specimen is fixed to the solid phase by the mediation of the derivative of the present invention.

Step 2:

No particular limitation is imposed on the detection method for $\beta_2$-GPI included in the complex formed in Step 1. However, a substance which binds to $\beta_2$-GPI is preferably used.

Examples of the substance which binds to $\beta_2$-GPI include an antibody recognizing $\beta_2$-GPI. The antibody used herein may be a monoclonal antibody or a polyclonal antibody, and is appropriately selected in accordance with the purpose of the $\beta_2$-GPI assay, required precision and sensitivity, etc. In general, when a monoclonal antibody, particularly a monoclonal antibody specifically recognizing $\beta_2$-GPI, is used, noise caused by substances other than $\beta_2$-GPI can be reduced, and higher precision and sensitivity can be attained as compared with the case where a polyclonal antibody is used.

The antibody against $\beta_2$-GPI can be produced through a routine preparation method for a polyclonal antibody or a monoclonal antibody making use of $\beta_2$-GPI as an antigen. Alternatively, a known antibody recognizing $\beta_2$-GPI can also be used. Examples of such known monoclonal antibodies include EY2C9 (IgM) [36], WB-CAL-1 (IgG2a, κ) [37], and Cof-22 (IgG1, κ) [38]. Characteristics of these antibodies will be described in detail in the below-mentioned present example.

Such a "substance which binds to $\beta_2$-GPI" is preferably labeled with a labeling substance, from the viewpoint of easy detection.

Even when the "substance which binds to $\beta_2$-GPI" itself is not labeled with a labeling substance, a labeled substance which binds to the "substance which binds to $\beta_2$-GPI" may also be used.

No particular limitation is imposed on the labeling substances employed for the labeling, so long as the substances can label typical proteins. Examples include enzymes (e.g., peroxidase, alkalaine phosphatase, β-galactosidase, luciferase, and acetylcholine esterase), fluorescent dyes (e.g., fluorescein isothiocyanate (FITC)), chemical fluorescent substances (e.g., luminol), biotin, and avidin (including streptavidin). The labeling method is appropriately determined from known labeling methods suited for the labeling substance; e.g., the glutaraldehyde method, the periodate cross-linking method, the maleimide cross-linking method, the carbodiimide method, and the activated ester method (see Chemistry of Proteins (part 2), published by Tokyo Kagaku Dojin, 1987). For example, when biotin is used as a labeling substance, a method employing a biotin hydrazide derivative (see Avidin-Biotin Chemistry: A Handbook, p. 57–63, published by PIERCE CHEMICAL COMPANY, 1994) is appropriately employed. When fluorescein isothiocyanate is used, a method disclosed in Japanese Patent Publication (kokoku) No. 63-17843 or a similar method is appropriately employed.

In the case where an antibody (not labeled) against $\beta_2$-GPI is employed as the substance which binds to $\beta_2$-GPI, another antigen (labeled) which binds to the corresponding antibody (immunoglobulin) can be employed as a secondary antibody. More specifically, when EY2C9 is used, an anti-human-IgM antibody which has been labeled with a labeling substance can be used, whereas when WB-CAL-1 or Cof-22 is used, an anti-mouse IgG antibody labeled with a labelling substance can be used. Examples of the labeling substance include horseradish peroxidase (HRP). Commercial products of such a secondary antibody can be used.

By detecting a labeling substance which has been bound to $\beta_2$-GPI by the mediation of the "substance which binds to $\beta_2$-GPI," $\beta_2$-GPI included in the complex formed in Step 1 can be detected.

The detection method can be appropriately determined by a person skilled in the art, in accordance with the labeling substance used. For example, when a peroxidase is employed as a labeling substance, hydrogen peroxide and a coloring substrate such as tetramethylbenzidine serving as a substrate for the enzyme are added to the enzyme reaction system, and the degree of coloring of the product can be detected by measuring the change in absorbance. When a fluorescent substance or chemiluminescent substance is used, detection can be performed by measuring fluorescence or luminescence provided from the solution after completion of reaction.

In the present specification, the term "detection" refers not only to qualitative detection (i.e., detection to check the presence or absence of the substance to be detected), but also to quantitative detection (i.e., detection to determine the amount (concentration) of the substance to be detected). The same convention is also applied to the term "assay" in the present specification.

When quantitative detection (assay) is performed, a calibration curve representing the relationship between the $\beta_2$-GPI concentration and certain detected values (e.g., absorbance) of the standard substance is prepared in advance by use of a $\beta_2$-GPI standard solution of a known concentration. Then, a specimen having an unknown concentration of the substance to be detected is subjected to measurement, and the concentration can be determined from the detected values by use of the calibration curve.

The assay method 2 of the present invention can be provided by further modifying the assay method 1 of the present invention. In the assay method 2, a specimen is brought into contact with the "complex of $\beta_2$-GPI and the derivative of the present invention immobilized on the solid phase" formed in Step 1 of the assay method 1 of the present invention, and the antibody recognizing the "complex of $\beta_2$-GPI and the derivative of the present invention" contained in the specimen is assayed.

Specifically, the assay method 2 is an assay method for an antibody recognizing the "complex of $\beta_2$-GPI and the derivative of the present invention," characterized in that the method includes at least the following steps:

a step of forming a complex of the "$\beta_2$-GPI-cholesterol derivative complex" and an antibody recognizing the "$\beta_2$-GPI-cholesterol derivative complex" by bringing $\beta_2$-GPI and a specimen into contact with the solid phase (Step 1); and a step of detecting the antibody contained in the complex which has been formed in Step 1 (Step 2).

The steps will be described individually.

Step 1:

The aforementioned description regarding the solid phase of the present invention is also applicable herein.

The $\beta_2$-GPI to be brought into contact with the solid phase of the present invention may or may not be completely purified, and the degree of purification may be appropriately determined by a person skilled in the art in accordance with factors such as the desired sensitivity. However, purified $\beta_2$-GPI is preferably used. Purification of $\beta_2$-GPI can be performed through, for example, the method described in the below-mentioned example.

The same description as provided in relation to the assay method 1 of the present invention is also applied to the specimen to be brought into contact with the solid phase of the present invention. The same contact method as employed in the assay method 1 of the present invention is applied to the contact method for bringing $\beta_2$-GPI and the specimen into contact with the solid phase of the present invention. No particular limitation is imposed on the contact method, so long as the method ensures the chance to attain contact between $\beta_2$-GPI molecules and the molecules of the derivative of the present invention immobilized on the solid phase of the present invention and the chance to attain contact between the "complex of $\beta_2$-GPI and the derivative of the present invention" and the antibody molecules present in the specimen and recognizing the complex.

Similar to the assay method 1 of the present invention, after contact between the complex and the antibody has been attained, the system is preferably allowed to react for about one hour at, for example, 0 to 45° C., preferably 4 to 37° C., so as to sufficiently bind $\beta_2$-GPI to the derivative of the present invention immobilized on the solid phase and also to sufficiently bind the antibody present in the specimen to the "complex of $\beta_2$-GPI and the derivative of the present invention." The same description as provided in relation to washing or other operation after reaction performed in the assay method 1 of the present invention is also applied herein.

By bringing the specimen and $\beta_2$-GPI into contact with the solid phase of the present invention, $\beta_2$-GPI and the derivative of the present invention immobilized on the solid phase form a complex, and the antibody recognizing the "$\beta_2$-GPI-cholesterol derivative complex" contained in the specimen binds to the complex, whereby the antibody present in the specimen is fixed to the solid phase by the mediation of the complex of $\beta_2$-GPI and the derivative of the present invention.

Step 2:

No particular limitation is imposed on the detection method for the antibody included in the complex formed in Step 1. However, preferably, a substance which binds to the antibody present in a specimen is employed. Examples of the substance which binds to the antibody include an antibody recognizing an antibody (immunoglobulin) present in the specimen. For example, in the case of assay of an antibody present in human serum (autoantibody), an anti-human-IgG antibody can be employed as a secondary antibody.

The description provided with respect to the substance which binds to the antibody (e.g., secondary antibody) employed in the assay method 1 of the present invention applies herein mutatis mutandis. Similar to the assay method 1 of the present invention, the substance which binds to the antibody is preferably labeled with a labeling substance. The descriptions provided with respect to the assay method 1 of the present invention regarding the labeling substance employed as a label, the labeling method, and the detection method for the labeling substance apply herein mutatis mutandis.

<4> Detection Method of the Present Invention

The detection method of the present invention is a method for detecting a disease, characterized in that the method includes assaying an antibody present in blood and recognizing the "complex of $\beta_2$-GPI and the derivative of the present invention" through the assay method 2 of the present invention and correlating the amount of the antibody present in blood to the disease.

In the detection method of the present invention, firstly, an antibody recognizing the "complex of $\beta_2$-GPI and the derivative of the present invention" and present in blood is assayed through the assay method 2 of the present invention. The aforementioned assay method 2 of the present invention is also applied herein. Although the specimen used herein is a "blood," the specimen is not necessarily a whole blood, and other blood samples may be used so long as the samples reflect the amount of the antibody present in blood. Specifically, there may also be used a plasma or a serum derived from the blood, a diluted product thereof, or a product thereof modified within a degree so as not to affect the antibody present in the sample.

In the detection method of the present invention, secondly, a disease is detected by correlating, to the disease, the amount (concentration) of the antibody present in such a specimen. The "amount of the antibody" may be the aforementioned antibody level (an actually measured value) obtained by use of the calibration curve which has been prepared on the basis of the relationship between the concentration of the standard antibody product and certain detected values of the labeled substance. Alternatively, the "amount of the antibody" may be a ratio (a relative value) of the antibody level to the amount of antibody in blood of a healthy subject (a human not suffering the disease to be detected) which ratio is obtained without using the calibration curve.

The aforementioned antibody level increases in the presence of a certain disease. Therefore, when the blood antibody level is lower than that of a healthy subject, such a low level can be correlated to the state of "suffering the disease" or the state of "highly likely suffering the disease." When the blood antibody level is equal to that of a healthy subject, the level can be correlated to the state of "not suffering the disease" or the state of "less likely suffering the disease."

In addition to check whether a subject suffers a certain disease or not, the detection method of the present invention includes detection of the degree of suffering the disease. For example, in a person who periodically undergoes an assay of the blood antibody level, when the antibody level tends to increase, the tendency can be correlated to the state of "progress of the disease" or the state of "highly likely progress of the disease." In contrast, when the assayed antibody level tends to decrease, the tendency can be correlated to the state of "amelioration of the disease" or the state of "highly likely amelioration of the disease." When the assayed antibody level is constant, the constant amount can be correlated to the state of "no change in sickness (healthiness)" or the state of "highly likely no change in sickness (healthiness)."

The "disease" is preferably an antiphospholipid syndrome or thrombosis. The thrombosis is preferably arterial thrombosis.

<5> Kit of the Present Invention

The kit 1 of the present invention is an assay kit for $\beta_2$-GPI, characterized in that the kit comprises at least the following (A) and (B):

the solid phase of the present invention (A) and a substance binding $\beta_2$-GPI (B).

The kit 2 of the present invention is an assay kit for an antibody recognizing "the complex of $\beta_2$-GPI and the derivative of the present invention," characterized in that the kit comprises at least the following (A) and (B):

the solid phase of the present invention (A) and a substance binding to an antibody recognizing "the complex of $\beta_2$-GPI and the derivative of the present invention" (B).

The aforementioned description regarding the solid phase of the present invention is also applicable herein. The descriptions provided with respect to the assay methods 1 and 2 of the present invention apply, mutatis mutandis, to the substance binding to $\beta_2$-GPI and to the substance binding to an antibody recognizing "the complex of $\beta_2$-GPI and the derivative of the present invention." No particular limitation is imposed on the constitution of the assay kits 1 and 2 of the present invention, so long as each kit contains the aforementioned (A) and (B). The kits may further include, as an additional component, for example, a species of known concentration serving as a standard for preparing a calibration curve ($\beta_2$-GPI (kit 1) and an antibody recognizing "the complex of $\beta_2$-GPI and the derivative of the present invention" (kit 2)); a reagent for detecting a labeling substance; a reagent which labels the substance binding to $\beta_2$-GPI or which labels the substance binding to the antibody recognizing "the complex of $\beta_2$-GPI and the derivative of the present invention"; or a labeled substance thereof. In addition to these additional components, the kits may further contain, for example, a blocking substance, the aforementioned washing liquid, a specimen-diluting agent, or an enzymatic reaction-stopping agent.

These kit components may be placed separately in individual containers and can be stored until use thereof as a kit which can be used in accordance with the assay method of the present invention.

The assay of $\beta_2$-GPI by use of the kit 1 of the present invention can be performed in accordance with the assay method 1 of the present invention, and the assay of the antibody recognizing "the complex of $\beta_2$-GPI and the derivative of the present invention" by use of the kit 2 of the present invention can be performed in accordance with the assay method 2 of the present invention.

The kit 2 of the present invention is preferably a kit for detecting a disease. The disease is preferably an antiphospholipid syndrome or thrombosis. The thrombosis is preferably arterial thrombosis. In this case, the detection of a disease can be performed in accordance with the detection method of the present invention.

BRIEF DESCRIPTION OF THE DRAWINGS

FIG. 2. Binding of $\beta_2$-GPI and anti-$\beta_2$-GPI autoantibodies to plasma LDLs or their lipid extracts:
A: Plasma LDLs, $\beta_2$-GPI, and mouse anti-human $\beta_2$-GPI monoclonal antibody (Cof-22) were sequentially incubated in a plate coated with Fab fragment of anti-apoB100 monoclonal antibody (1D2). Binding was detected using HRP-labeled anti-mouse IgG.
B to D: Lipid extracts from LDLs were applied to a plate. $\beta_2$-GPI binding was detected using Cof-22 and using HRP-labeled anti-mouse IgG (B). Subsequent binding of WB-CAL-1 (C) and EY2C9 (D) were detected using HRP-labeled anti-mouse IgG (C), and with HRP-labeled anti-human IgM (D), respectively. Open columns: without $\beta_2$-GPI, closed columns: with $\beta_2$-GPI (C, D). Data are indicated as the mean± SD of triplicate samples.

Scraped Band-1 was eluted on Sephacil-Peptide column and detected at 210 nm (A) and 234 nm (B). Data of ligand blot analysis on eluate using EY2C9 are also shown in (C).

Figure 5:
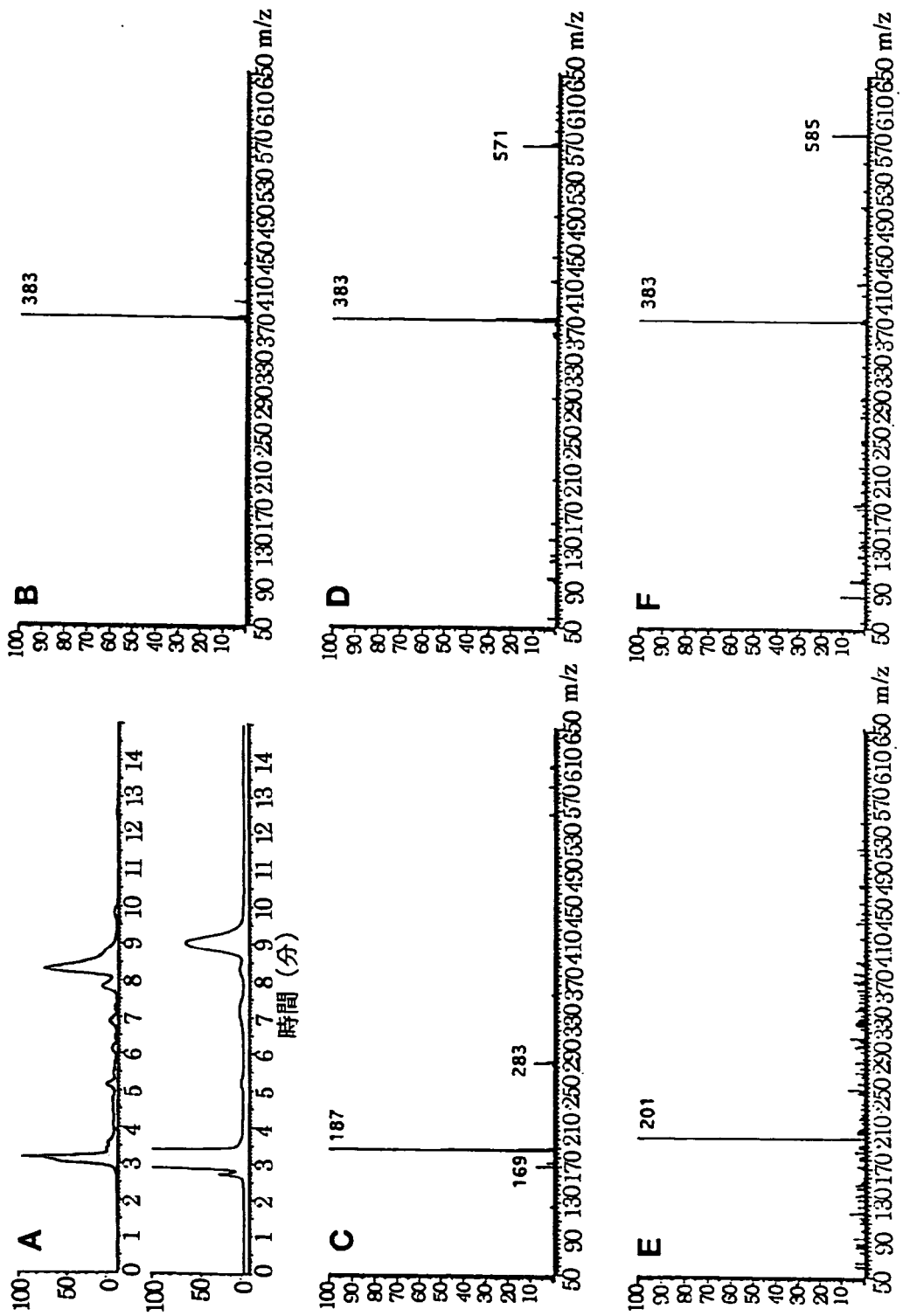

FIG. 5. LC/MS of purified oxLig-1 and its methylated compound.
A: HPLC profiles of oxLig-1 (upper) and methylated oxLig-1 (lower) at 234 nm.
B: A positive ionization mass spectrum of 7-ketocholesterol.
C: A negative ionization mass spectrum of oxLig-1.
D: A positive ionization mass spectrum of oxLig-1.
E: A negative ionization mass spectrum of methylated oxLig-1.
F: A positive ionization mass spectrum of methylated oxLig-1.

Figure 6:
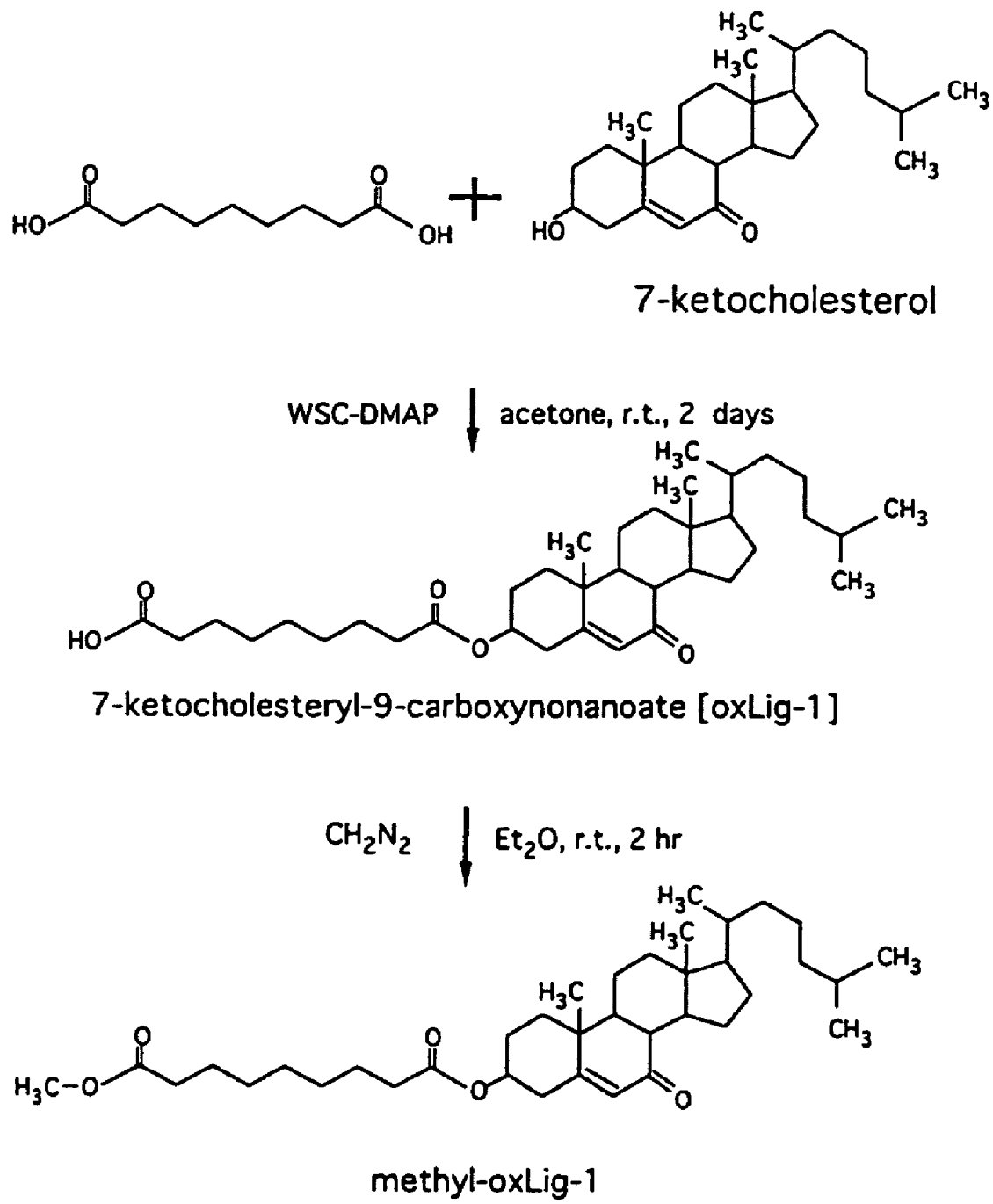

FIG. 6. Synthesis of oxLig-1 (9-oxo-9-(7-ketocholest-5-en-3$\beta$-yloxy)nonanoic acid) and its methylation.

Figure 7:
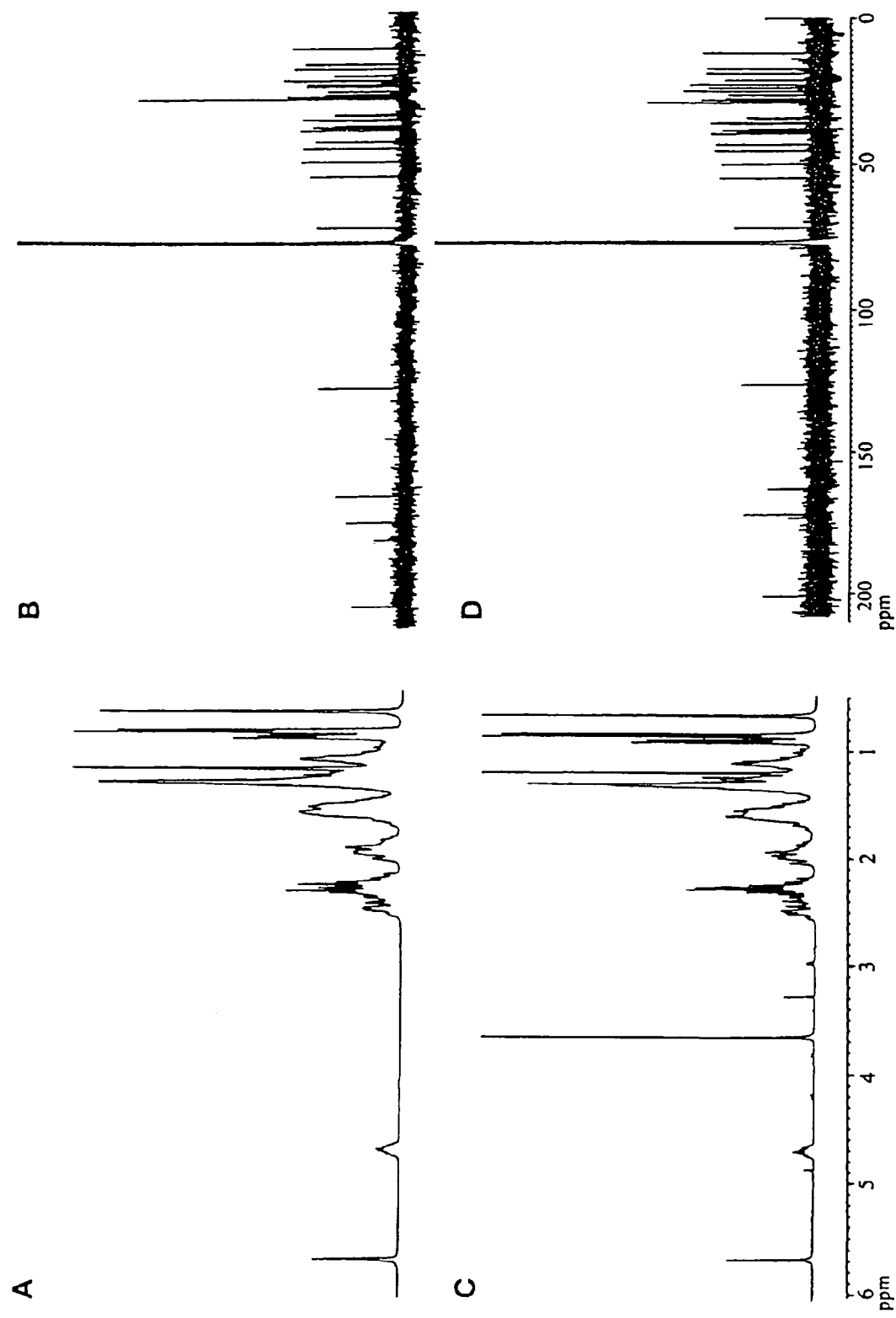

FIG. 7. Nuclear magnetic resonance (NMR) spectrum of synthesized oxLig-1 and its methylated compound. 300 MHz $^1$H-NMR spectra of synthesized oxLig-1 (A) and of methylated oxLig-1 (C). 75.3 MHz $^{13}$C-NMR spectra of synthesized oxLig-1 (B) and of methylated synthesized oxLig-1 (D).

Figure 8:
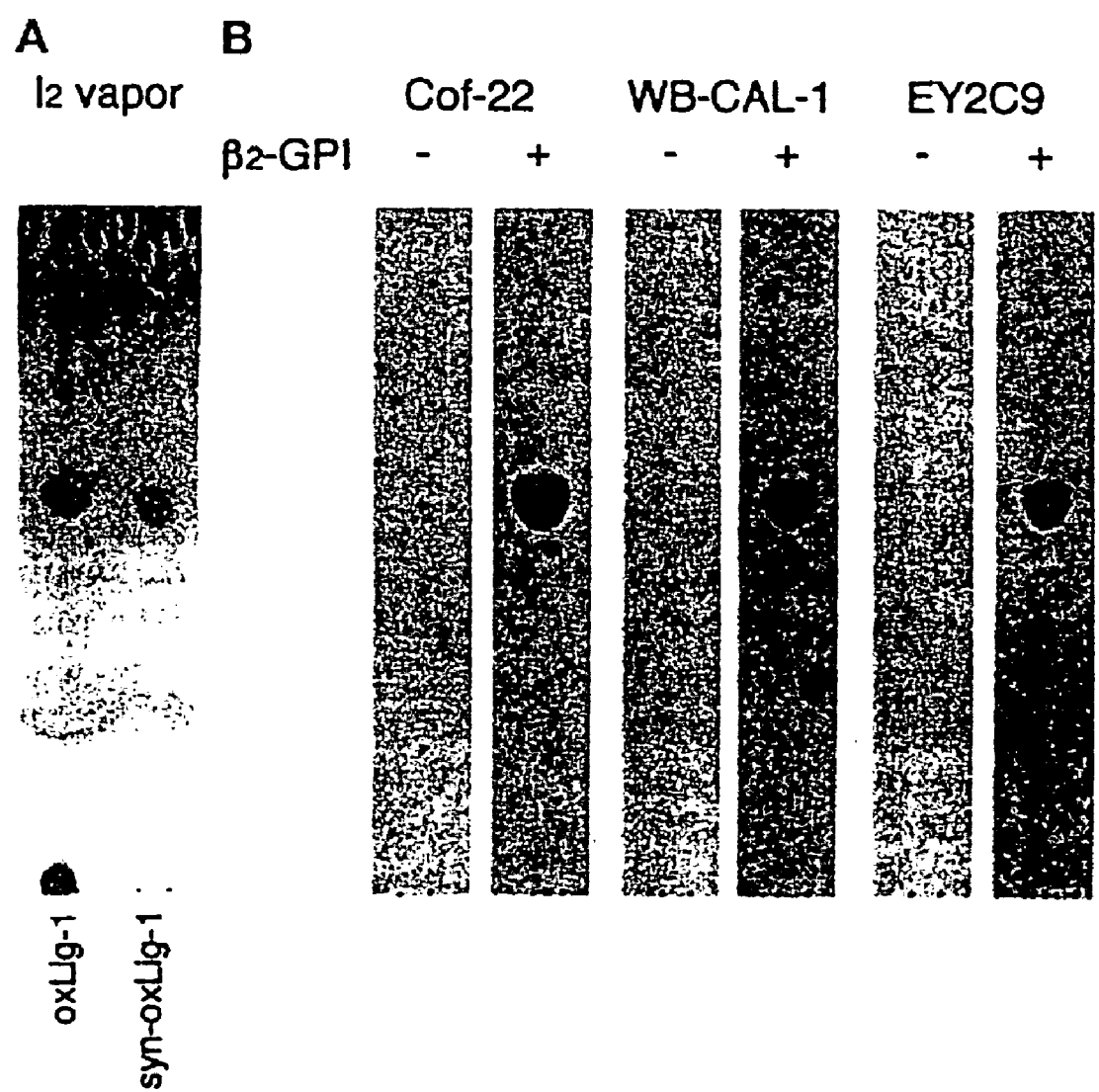

FIG. 8. TLC and ligand blot analysis on synthesized oxLig-1.
A: oxLig-1 and synthesized oxLig-1 was spotted on a TLC plate, developed with solvent A, and detected with $I_2$-vapor.
B: Ligand blot of synthesized oxLig-1 was performed with anti-$\beta_2$-GPI antibodies in the presence (+) or absence (−) of $\beta_2$-GPI.

Figure 9:
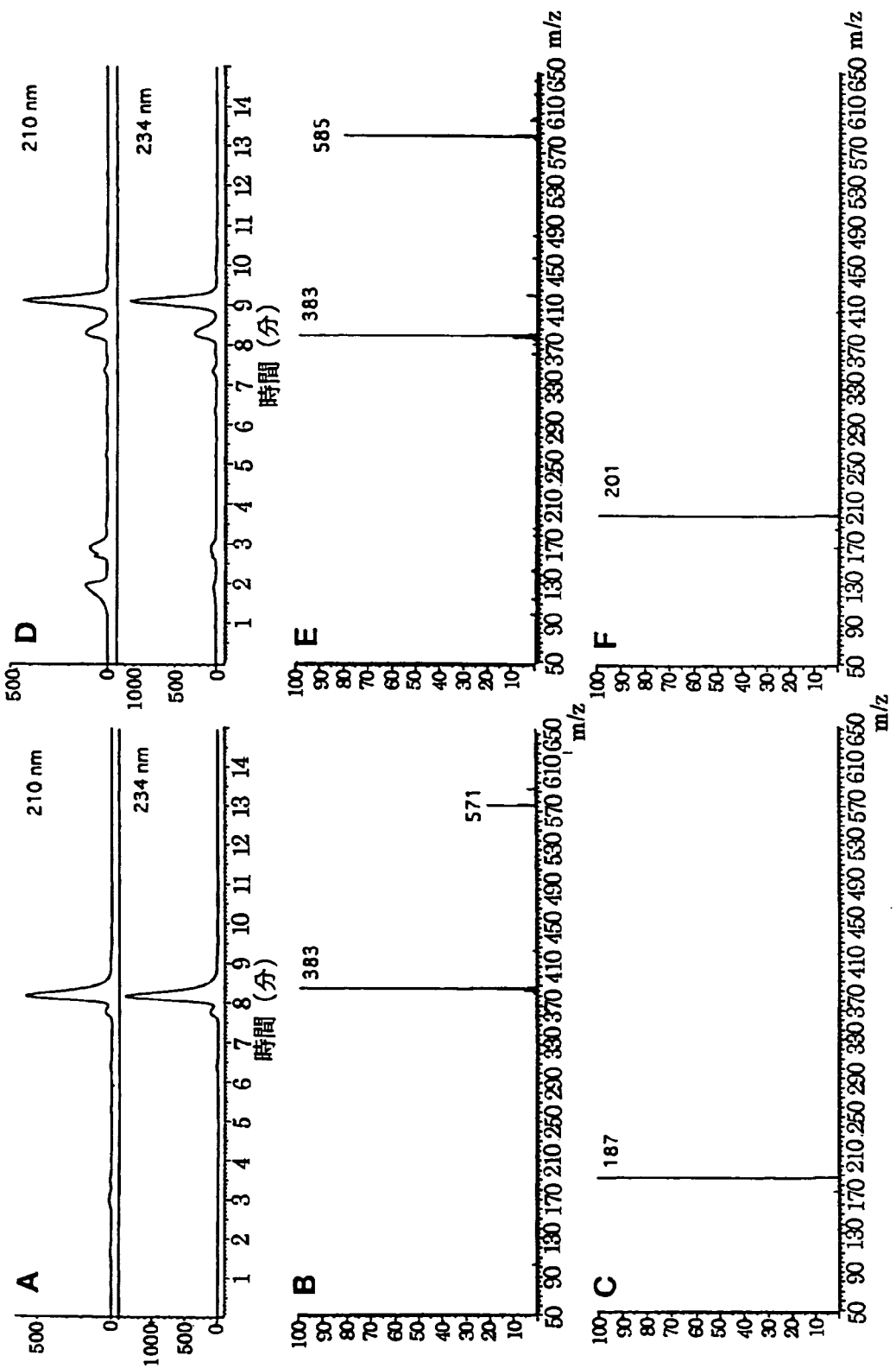

FIG. 9. LC/MS of synthesized oxLig-1 and its methylated compound.
A: LC chromatograms of synthesized oxLig-1 at 210 nm and at 234 nm.
B: A positive ionization mass spectrum of synthesized oxLig-1.
C: A negative ionization mass spectrum of synthesized oxLig-1.
D: LC chromatograms of methylated synthesized oxLig-1 at 210 nm and at 234 nm.
E: A positive ionization mass spectrum of methylated oxLig-1.
F: A negative ionization mass spectra of methylated synthesized oxLig-1.

Figure 10:
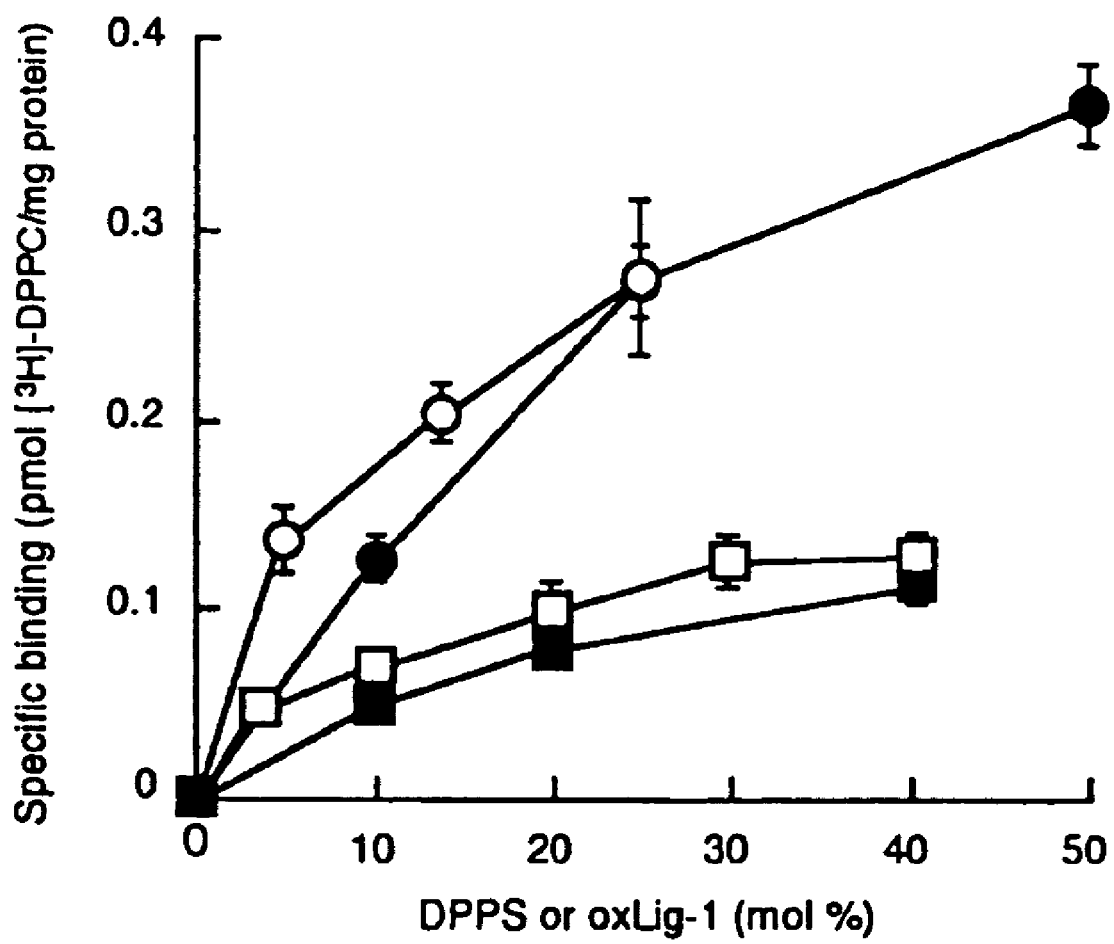

FIG. 10. Effect of phosphatidylserine (PS) or oxLig-1 content on the binding of liposomes to macrophages. A monolayer of J774.A1 cells was incubated for 2 hours at 4° C. with Celgrosser-P medium containing $^3$H-labeled liposomes (50 nmol lipid/well). Open circle represents PS-liposomes; closed circle represents PS-Chol-liposomes; open square represents oxLig-1-liposomes; and closed square represents oxLig-1-Chol-liposomes. Data are indicated as the mean± SD of triplicate samples.

FIG. 11. $\beta_2$-GPI and anti-$\beta_2$-GPI monoclonal antibody-dependent binding of ligand-containing liposomes to macrophage. A monolayer of J774.A1 cells was incubated for 2 hours at 4° C. with Celgrosser-P medium containing $^3$H-labeled liposomes (50 nmol lipid/well) and WB-CAL-1, in the presence or absence of $\beta_2$-GPI (200 µg/ml).
A: Binding of PS-liposomes (PS: 50 mol %,) to J774.A1. cells in the presence (closed square) or absence (open square) of $\beta_2$-GPI (200 µg/ml)
B: Binding of oxLig-1-liposomes (oxLig-1: 40 mol %) to J774.A1 cells in the presence (black bar) or absence (white bar) of $\beta_2$-GPI (200 µg/ml).
C: A monolayer of J774.A1 cells was incubated for 2 hours at 4° C. with Celgrosser-P medium containing $^3$H-labeled synthesized oxLig-1-liposomes (50 nmol lipid/well) and WB-CAL-1, in the presence or absence of $\beta_2$-GPI (200 µg/ml). Binding of synthesized oxLig-1-liposomes in the absence of $\beta_2$-GPI and WB-CAL-1 (open circle), binding of synthesized oxLig-1-liposomes in the presence of $\beta_2$-GPI (open square), binding of synthesized oxLig-1-liposomes in the presence of WB-CAL-1 (closed square), and binding of synthesized oxLig-1-liposomes in the presence of both $\beta_2$-GPI and WB-CAL-1 (closed circle). Data are indicated as the mean ± SD of triplicate samples.

Figure 12:
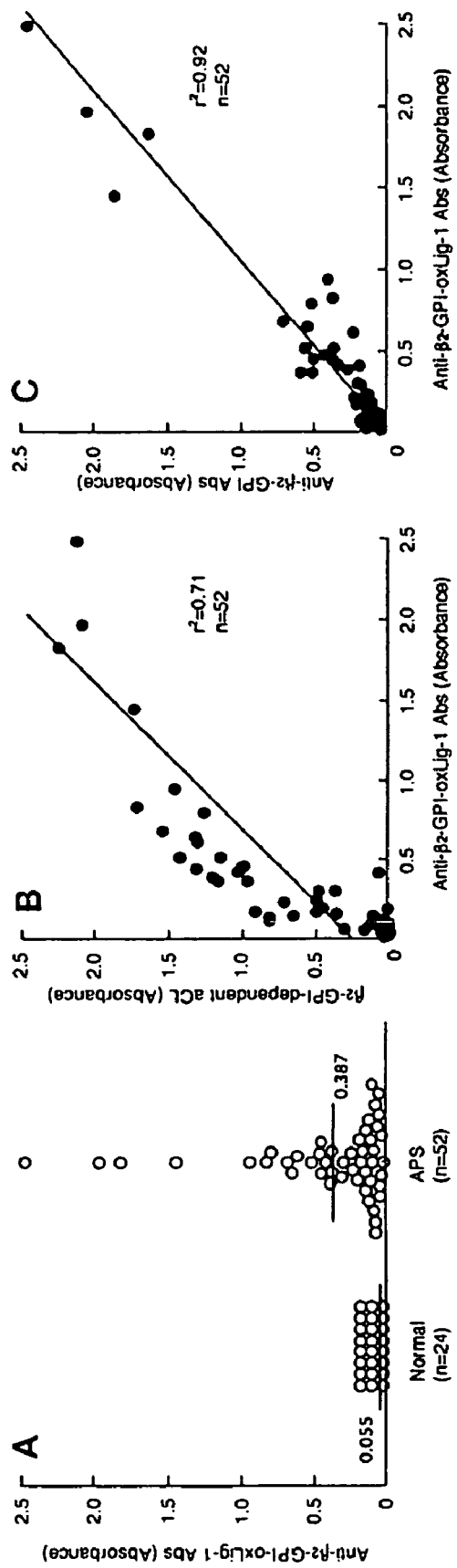

FIG. 12. Autoantibodies present in APS serum samples against solid phase $\beta_2$-GPI-oxLig-1 complex. Serum samples were obtained from healthy subjects (n=24) and APS patients with episodes of thrombosis (n=52).
A: Antibody values in individual serum samples
B: Relationship between anti-$\beta_2$-GPI-oxLig-1 antibody values and $\beta_2$-GPI-dependent aCL values
C: Relationship between anti-$\beta_2$-GPI-oxLig-1 antibody values and anti-$\beta_2$-GPI antibody values.

Figure 13:
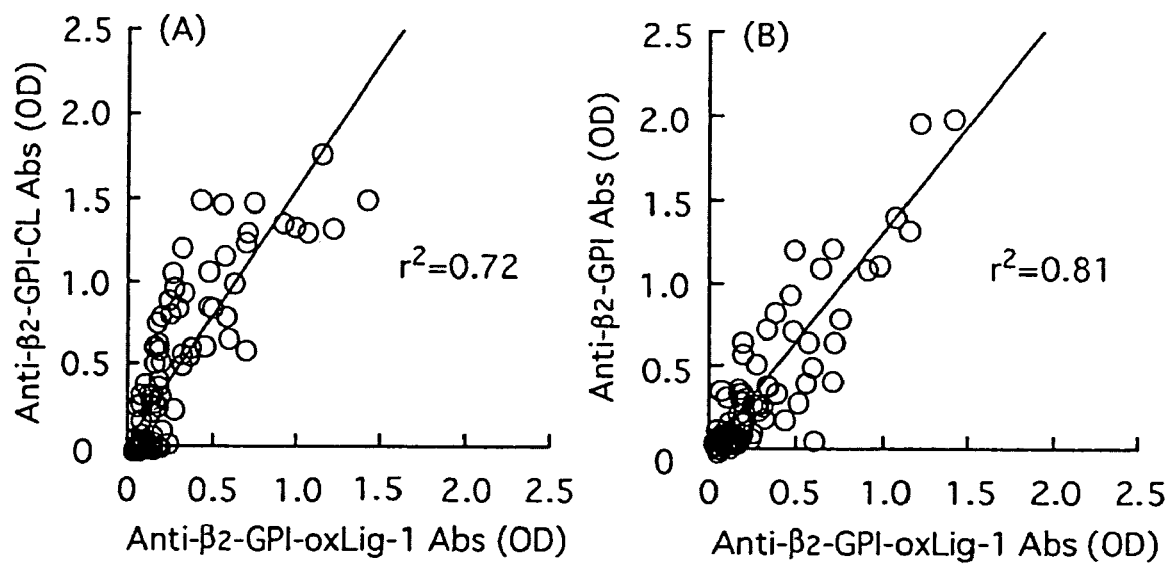

FIG. 13. Relationship between anti-$\beta_2$-GPI-oxLig-1 antibody values and antibody values of the $\beta_2$-GPI-dependent aCL (anti-$\beta_2$-GPI-CL antibody) in ELISA, and relationship between anti-$\beta_2$-GPI-oxLig-1 antibody values and anti-$\beta_2$-GPI antibody values in ELISA. Plasma samples of 133 APS and/or SLE patients (87 APS patients and 47 SLE only patients) were assayed through the method described in relation to materials and methods.

Figure 14:
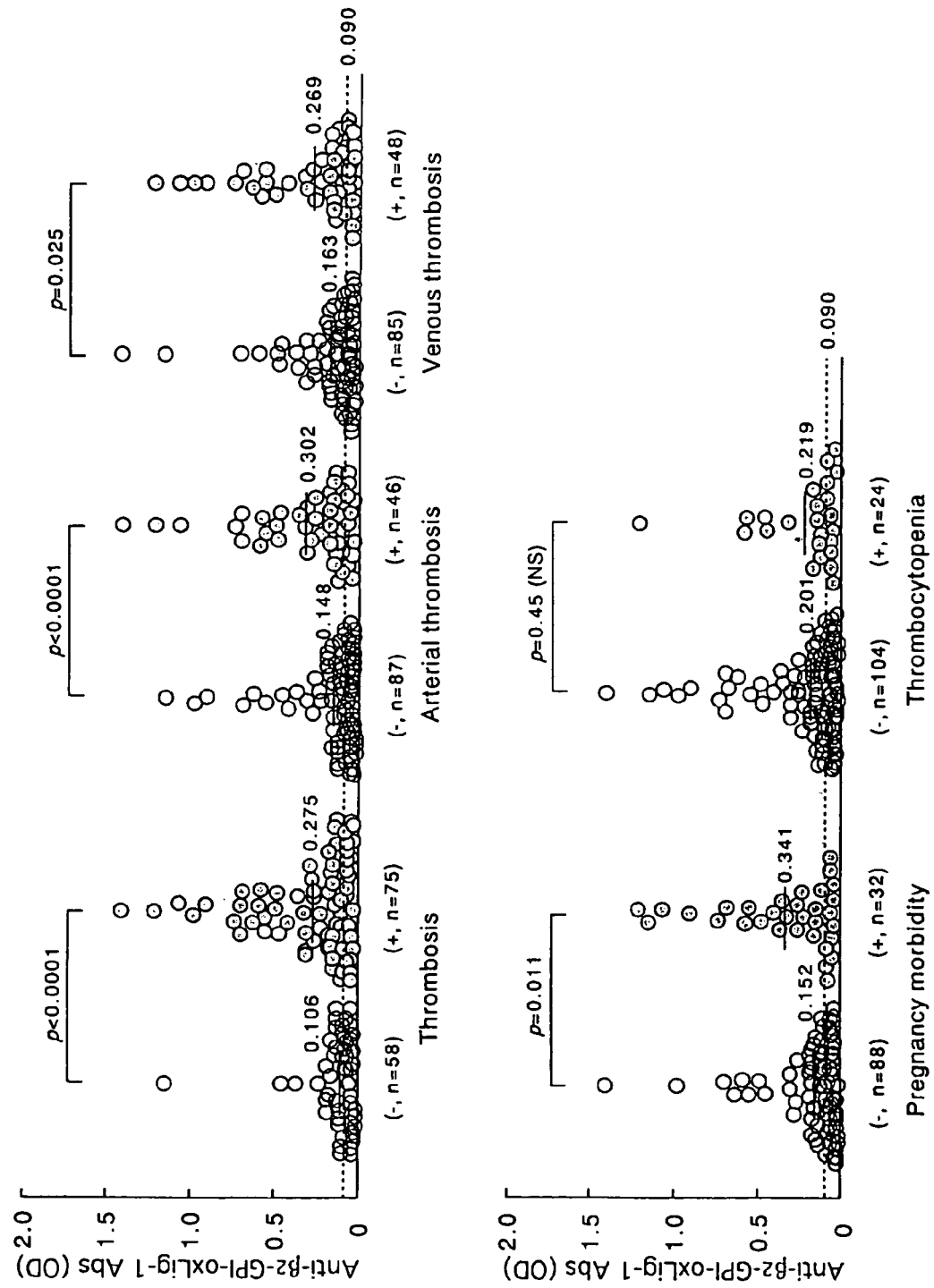

FIG. 14. Relationship between antibody values and clinical episodes. Plots of anti-$\beta_2$-GPI-oxLig-1 antibody values of APS and/or SLE patients (without clinical episodes (open circles), with clinical episodes (gray circles)). The values of p represent Mann-Whitney U-test results. The dashed lines represent a cut-off value (the level exceeding the averaged (healthy control) antibody value by 3×SD).

FIG. 15. TLC and Ligand blot profiles of oxLig-2, Me-oxLig-2, 13-COOH-7KC, and Me-13-COOH-7KC.

Figure 16:
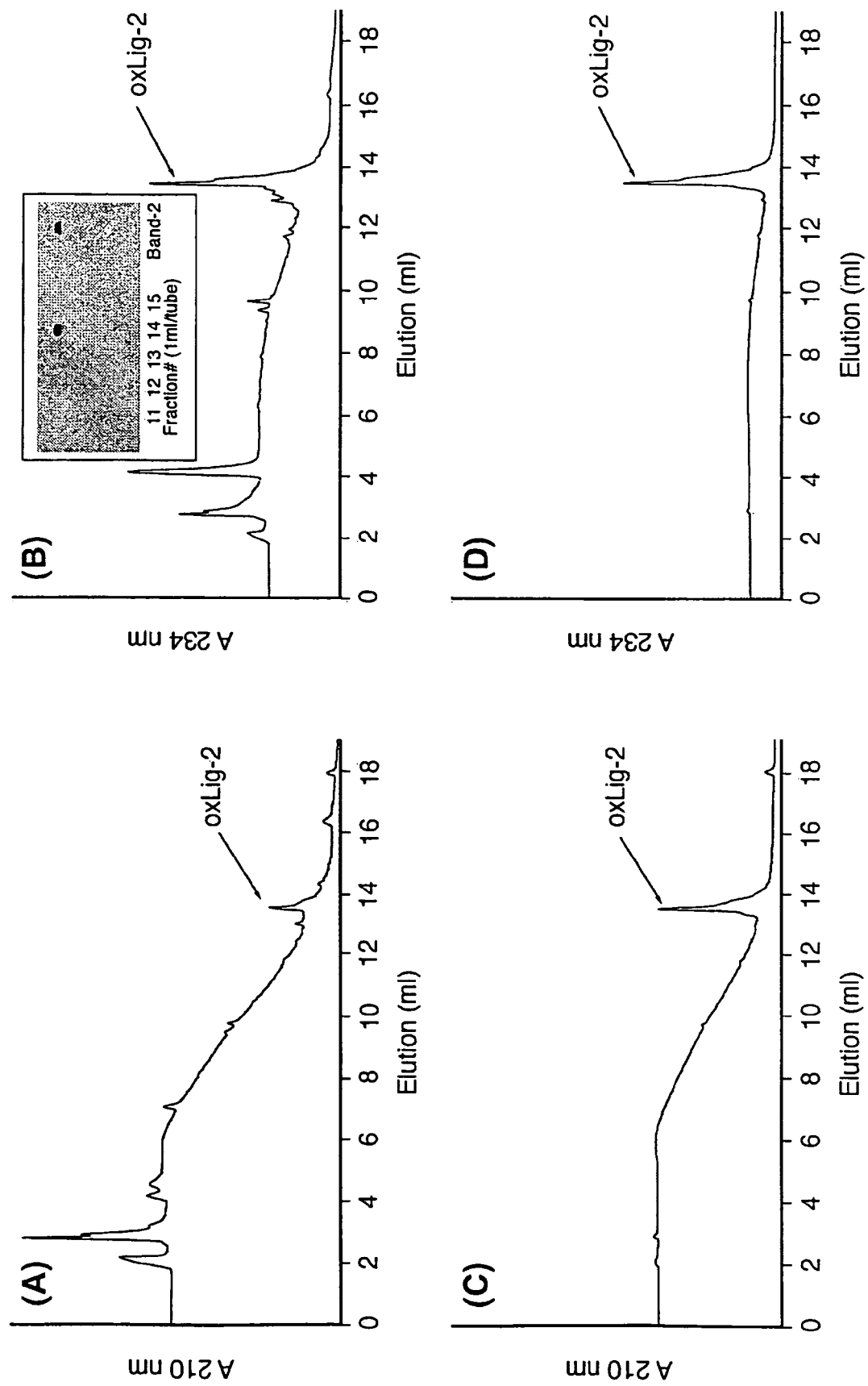

FIG. 16. Elution profiles of Band-2 obtained by reversed phase high performance liquid chromatography (HPLC). Scraped Band-2 was eluted on Sephacil-Peptide column and detected at 210 nm (A) and 234 nm (B). Data of ligand blot analysis on eluate using EY2C9 are also shown in (B). Fraction 14 was purified again through HPLC under the same conditions so as to confirm the purity (C and D).

Figure 17:
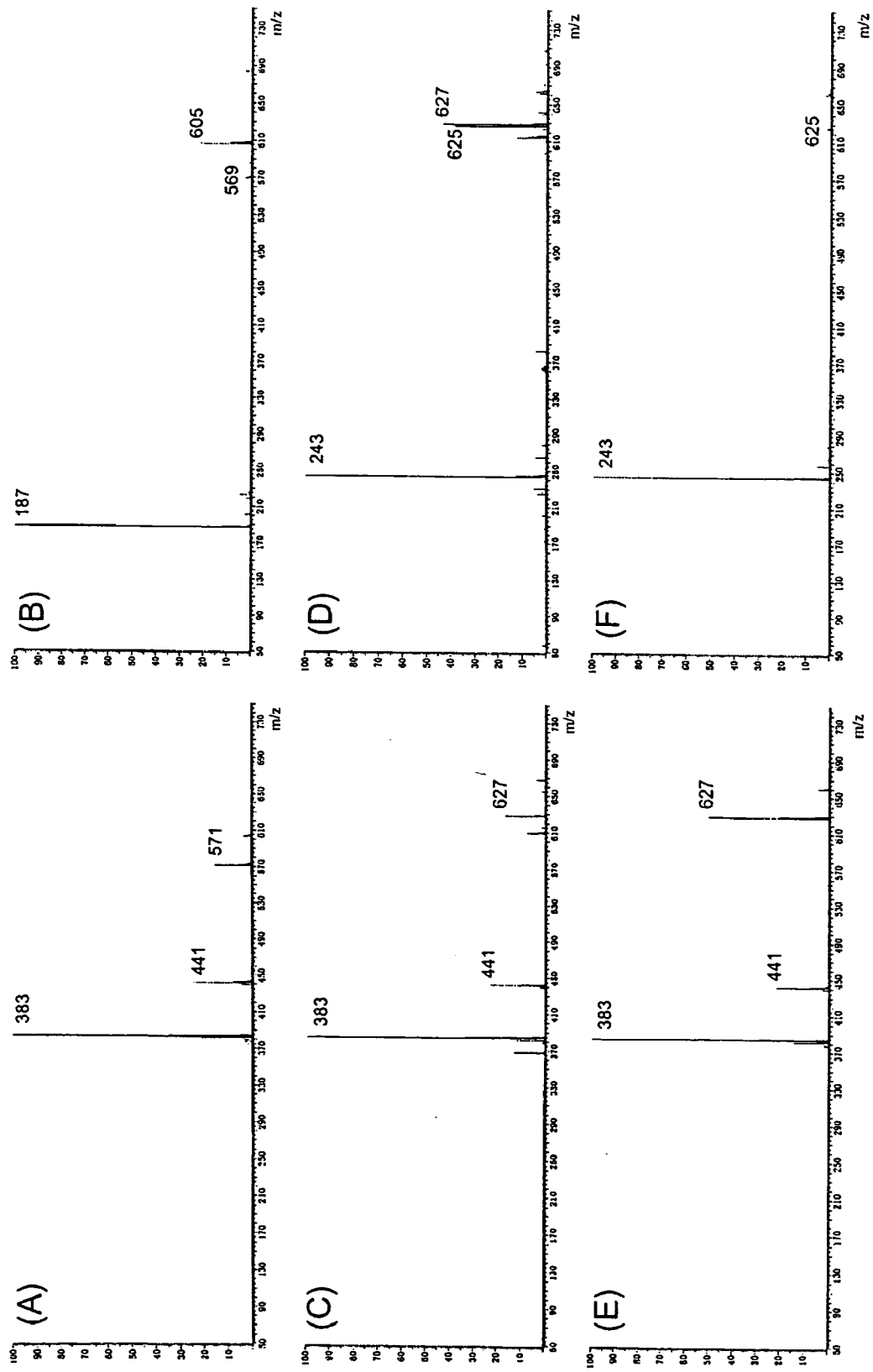

FIG. 17. LC/MS of purified or synthesized $\beta_2$-GPI ligands. Positive ionization mass spectra of oxLig-1 (A), oxLig-2 (C), and 13-COOH-7KC (E) (left column) and negative ionization mass spectra of oxLig-1 (B), oxLig-2 (D), and 13-COOH-7KC (F) (right column).

FIG. 18. Structures of cholesteryl esters serving as $\beta_2$-GPI ligands.
Structures of cholesteryl linoleate (A), oxLig-1 (B), oxLig-2 (C), and 13-COOH-7KC (E). Schemes of fragmentation possibly occurring in mass spectroscopy are specified by means of arrows. Scission at each arrow position will result in formation of the corresponding fragment ion "D."

Figure 19:
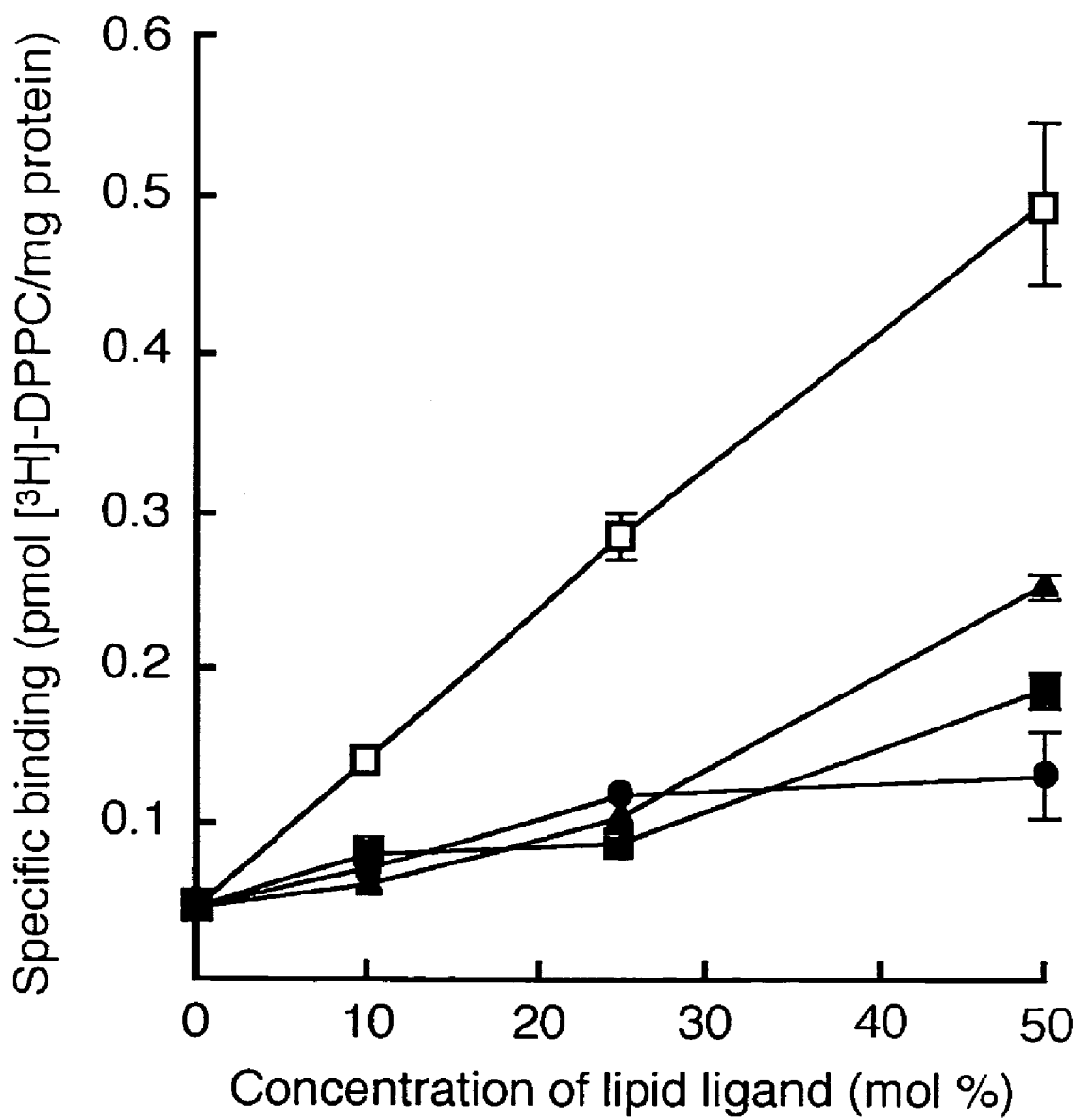

FIG. 19. Direct binding of ligand-containing liposomes to macrophage.
A monolayer of J774.A1 cells was incubated for 2 hours at 4° C. with Celgrosser-P medium containing [$^3$H]-labeled liposomes (containing a predetermined ligand, 50 nmol lipid/well). DPPS-containing liposomes (open squares), oxLig-1-containing liposomes (closed squares), oxLig-2-containing liposomes (closed circles), and 13-COOH-7KC-containing liposomes (closed triangles). Data are indicated as mean± SD of triplicate samples.

Figure 20:
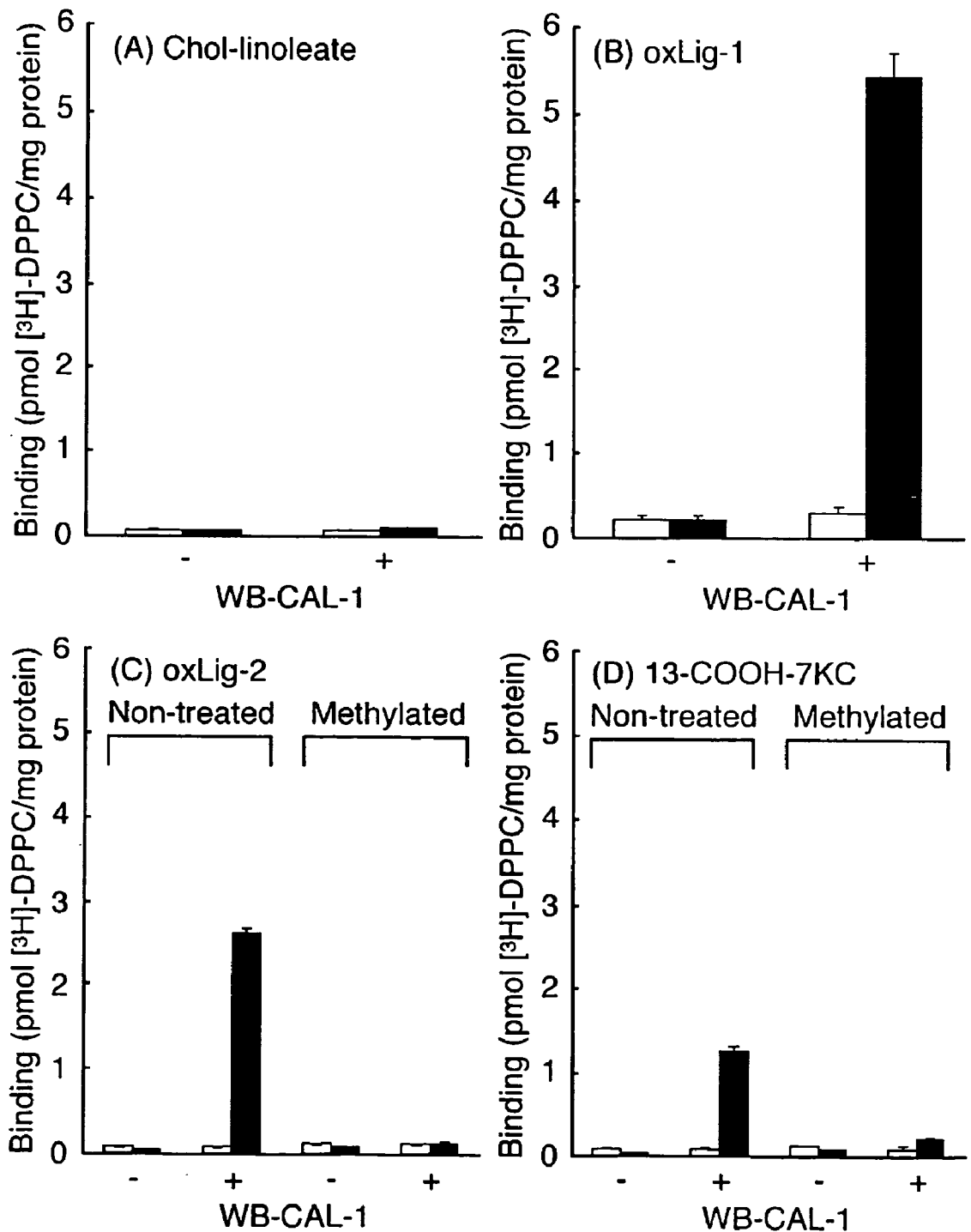

FIG. 20. $\beta_2$-GPI and anti-$\beta_2$-GPI antibody-dependent binding of ligand-containing liposomes to macrophage.

A monolayer of J774.A1 cells was incubated for 2 hours at 4° C. with Celgrosser-P medium containing [$^3$H]-labeled liposomes (containing a predetermined ligand (30 mmol %), 50 nmol lipid/well) and in the presence (black bars) or absence (white bars) of $\beta_2$-GPI (200 µg/mL) and WB-CAL-1 (200 µg/mL).
Chart A: Cholesteryl linoleate-containing liposomes; Chart B: oxLig-1-containing liposomes, Chart C: oxLig-2-containing liposomes; and Chart D: 13-COOH-7KC-containing liposomes. In Charts C and D, comparison was made with methylated ligand-containing liposomes. Data are indicated as mean± SD of triplicate samples.

BEST MODE FOR CARRYING OUT THE INVENTION

The present invention will next be described in more detail by way of example, which should not be construed as limiting the invention thereto.

<1> Materials and Methods
Firstly, materials and methods employed in the present example will be described.

(1) Chemicals
L-α-Dipalmitoylphosphatidylserine (DPPS), CL, Chol, and 7-ketocholesterol (5-cholesten-3β-ol-7-one) were obtained from Sigma Chemical Co. PAPC and DOPC from Avanti Polar Lipids Inc. [$^3$H]DPPC (80 Ci/mmol) from Amersham-Pharmacia Biotech. Other chemicals were obtained from commercial sources and of reagent grade quality.

(2) Purification of Human $\beta_2$-GPI
$\beta_2$-GPI was purified from normal human plasma as described in [35] with slight modification. Pooled plasma from healthy subjects were chromatographed on a heparin-Sepharose column (or CL-polyacrylamide gel column), on a DEAE-cellulose column, and on an anti-$\beta_2$-GPI affinity column. To remove any contamination by IgGs, the $\beta_2$-GPI-containing fraction was further passed through a protein A-Sepharose column. The final $\beta_2$-GPI fraction was delipidated by extensive washing with n-butanol.

(3) Anti-$\beta_2$-GPI Positive Serum Samples were Obtained from APS Patients with Episodes of Arterial Thrombosis.
To eliminate endogenous $\beta_2$-GPI in some experiments, serum samples were passed through a heparin-Sepharose column. The effluent was dialyzed against PBS and was used for ELISAs.

(4) Monoclonal Antibodies (mAbs)
EY2C9 (IgM): A human monoclonal anti-$\beta_2$-GPI autoantibody, established from peripheral blood lymphocytes from an APS patient [36].
WB-CAL-1 (IgG2a, κ): A mouse monoclonal anti-$\beta_2$-GPI autoantibody, derived from an (NZW×BXSB) F1 mouse [37].
Cof-22 (IgG1, κ): A monoclonal anti-human β2-GPI antibody, established from BALB/c mice immunized with human $\beta_2$-GPI [38].
Both EY2C9 and WB-CAL-1 bind either to a complex of $\beta_2$-GPI and CL and to $\beta_2$-GPI adsorbed on an oxygenated polystyrene plates. In contrast, Cof-22 is specific for human $\beta_2$-GPI and recognizes its native structure.

(5) Preparation of oxLDL and Lipid Extraction
Plasma LDL (1.019<d<1.063 g/mL) was isolated by ultracentrifugation from fresh normal human plasma, as described in [39]. LDL (100 µg protein/mL) was oxidized by incubating with 5 µM CuSO$_4$ (PBS solution) for 8 hours at 37° C. To stop the oxidation, 1 mM EDTA was added. The oxidized sample was extensively dialyzed against PBS containing 1 mM EDTA.

Protein concentration was determined using BCA protein assay reagent (product of Pierce Chemical Co.). An aliquot of a sample was taken to determine thiobarbituric acid reactive substance (TBARS) value serving as an index of an extent of oxidation [40], and for use in agarose gel electrophoresis. A lipid fraction was extracted from LDLs according to the method described in [41].

(6) Assay for Molecular Interaction

Real-time molecular analysis was performed using an optical biosensor, IAsys (product of Affinity Sensors).

Binding of $\beta_2$-GPI to LDLs or liposomes: Biotinyl-$\beta_2$-GPI was immobilized on a biotinyl-cuvette via streptavidin. LDLs or liposomes at various concentrations were placed in the cuvette. Antibodies binding to LDLs or liposomes: The biotinyl-WB-CAL-1 was immobilized on the cuvette. LDLs or liposomes were added at various concentrations in the presence (10 µg/mL) or absence of $\beta_2$-GPI.

(7) ELISA for Detecting Binding of $\beta_2$-GPI to Anti-$\beta_2$-GPI Antibody

Binding to LDLs: A microtiter plate (Immulon 2HB, Dynex Technologies Inc.) was coated with 50 µL of F(ab')2 of 1D2 (anti-apoB 100 antibody; 10 µg/mL, product of Yamasa Corp.) by incubation overnight at 4° C. After blocking with PBS containing 1% skim milk, the plate was incubated with LDLs for one hour. The wells were incubated sequentially with $\beta_2$-GPI (15 µg/mL), Cof-22, and horseradish peroxidase (HRP)-labeled anti-mouse IgG, each for one hour. The color was developed with H$_2$O$_2$ and o-phenylenediamine, and OD was measured at 490 nm.

Binding to extracted lipids: A microtiter plate (Immulon 1B, Dynex Technologies Inc.) was coated with lipids extracted from LDLs (50 µg/mL, 50 µL/well) by ethanol evaporation. The wells were blocked with PBS containing 1% BSA for one hour and the wells were incubated with 30 µg/mL of $\beta_2$-GPI for one hour. Then, $\beta_2$-GPI binding was detected using Cof-22 and HRP-labeled anti-mouse IgG antibodies. Alternatively, an anti-$\beta_2$-GPI autoantibody (Cof-22, WB-CAL-1, or EY2C9) was diluted with a 0.3% BSA-containing PBS, and the diluted antibody was added to the coated plate (1.0 µg/mL, 100 µL/well) and incubated with $\beta_2$-GPI (15 µg/mL) for one hour. The binding of the antibody was detected by an HRP-labeled anti-mouse IgG /or an anti-human IgM. The color was developed with H$_2$O$_2$ and o-phenylenediamine, and OD was measured at 490 nm. Between these steps, extensive washing were done using PBS containing 0.05% Tween 20.

(8) Thin Layer Chromatography (TLC) and Ligand Blot Analysis

Extracted lipids were spotted on a Polygram silica gel plate (product of Machery-Nagel) and developed in chloroform/methanol/30% ammonia/water (120:80:10:5, v/v/v/v, hereinafter referred to as solvent A). The plate was stained with I$_2$ vapor, or with a spray of molybdenum blue, of 2N sulfuric acid containing 2% orcin, or of glacial acetic acid/sulfuric acid (19:1, v/v) (Lieberman-Burchard reaction). Alternatively, the developed plate was subjected to ligand blot with $\beta_2$-GPI and an anti-$\beta_2$-GPI antibody. TLC plates were blocked with PBS containing 1% bovine serum albumin (BSA) and were subsequently incubated with $\beta_2$-GPI, anti-$\beta_2$-GPI antibodies (Cof-22, WB-CAL-1, or EY2C9), and HRP-labeled anti-mouse IgG antibodies or anti-human IgM antibodies for one hour. In each step, plates were extensively washed with PBS. The color was developed with H$_2$O$_2$ and 4-methoxy-1-naphtol (product of Aldrich). The ligand-enriched bands scraped from the TLC plate were subjected to another TLC in chloroform/methanol (8:1, v/v) (hereinafter referred to as solvent B). For large scale purification of the ligand, extracted lipids were loaded on a TLC silica gel 60 plate (PLC plate; product of Merck) of 2 mm thickness.

(9) HPLC

A fraction rich in a ligand (originating from oxLDL) obtained by two-step TLC was analyzed by reversed phase HPLC on a Sephasil Peptide C-18 5-µm column (4.6 mm×250 mm; product of Amersham-Pharmacia Biotech). The column underwent elution with a mixture of acetonitrile/isopropanol/water (60:30:2, v/v/v, hereinafter referred to as solvent C) at a flow rate of 0.5 mL/min and fractionated every minute. Each eluate was spotted on a TLC plate and subjected to ligand blot with $\beta_2$-GPI and EY2C9.

(10) NMR $^1$H-NMR and $^{13}$C-NMR spectra were recorded by means of ASX-300 spectrometer (Bruker).

(11) Mass Spectroscopy

Synthesized oxLig-1 was analyzed on a Shim-pack VP-ODS column (4.6 mm×150 mm) with an LC/MS-QP8000α (Shimadzu Corp.), using solvent C (LC/MS; liquid chromatography/mass spectroscopy). Positive and negative ionization mass spectra were recorded in the mass range of 50–850.

Mass spectrometry of oxLig-1, oxLig-2 purified from Band-2, and synthesized 13-COOH-7KC, which are $\beta_2$-specific ligands, was carried out on a Shim-pack FC-ODS column (4.6 mm×30 mm) with an LC/MS-2010 spectrometer (Shimadzu Corp.), using solvent F (30% acetone in methanol) and water with a linear gradation in concentration (50 to 100%). Positive and negative ionization mass spectra were taken in a mass range of 50 to 750.

The field desorption (FD) mass spectra of synthesized oxLig-1 and methylated oxLig-1 were recorded on JMS-SX102A and JMS AX-500 spectrometers (product of JEOL), respectively.

(12) Synthesis of $\beta_2$-GPI-Specific Ligand (oxLig-1)

Figure 1:
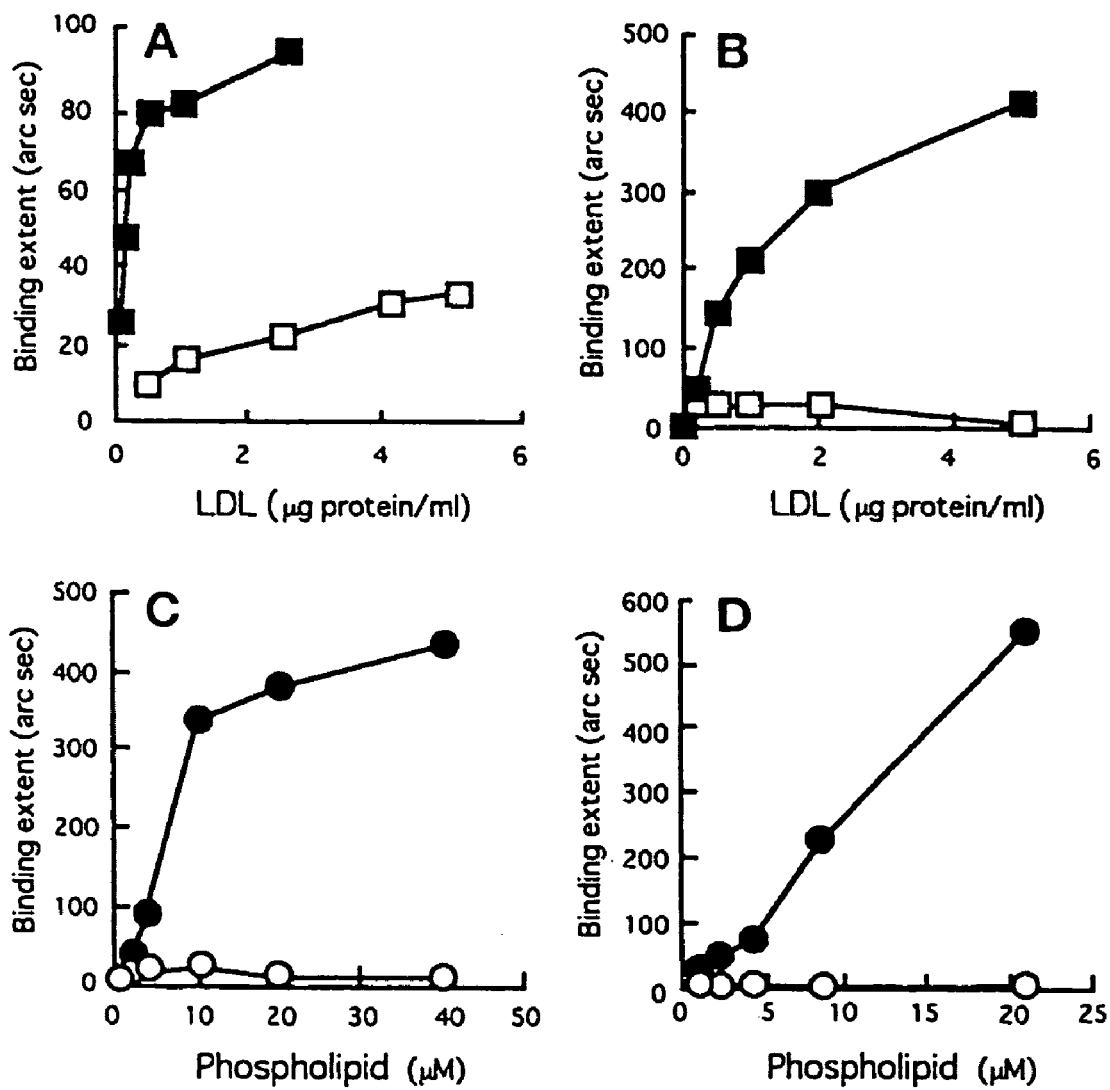
FIG. 1. Molecular interactions among $\beta_2$-GPI, LDLs, lipoproteins (PLs), and anti-$\beta_2$-GPI autoantibody, detected by an optical biosensor.
A: LDL (open square) or oxLDL (closed square) binding to solid phase $\beta_2$-GPI;
B: LDL (open square) or oxLDL (closed square) binding to solid phase WB-CAL-1 in the presence of $\beta_2$-GPI;
C: DOPE (open circle) or CL (closed circle) binding to solid phase $\beta_2$-GPI; and
D: DOPE (open circle) or CL (closed circle) binding to solid phase WB-CAL-1 in the presence of $\beta_2$-GPI.

The ligand, oxLig-1, was first isolated from Cu$^{2+}$-oxLDL through two steps of TLC, followed by HPLC, and finally identified as 9-oxo-9-(7-ketocholest-5-en-3$\beta$-yloxy) nonanoic acid (7-ketocholesteryl-9-carboxynonanoate) (FIG. 1). In the present example, the synthesized oxLig-1 was used instead of purified oxLig-1. To a solution of 7-ketocholesterol (5-cholesten-3$\beta$-ol-7-one, 50.1 mg, 0.125 mmol) and azelaic acid (70.6 mg, 0.375 mmol) in acetone (4 mL) were added 1-ethyl-3-(3-dimethylaminopropyl)carbodiimide hydrochloride (95.8 mg, 0.50 mmol) and 4-(dimethylamino)pyridine (30.5 mg, 0.25 mmol). The mixture was stirred at room temperature for two days, concentrated, and extracted with chloroform. The extract was successively washed with 2M hydrochloric acid and dried over magnesium sulfate anhydrate, and the solvent was evaporated. The residue was subjected to column chromatography on silica gel using toluene/ethyl acetate (3:1, v/v), to thereby yield oxLig-1 (36.0 mg, yield: 50.4%).

(13) Analysis Results of Synthesized oxLig-1

(NMR); $^1$H-NMR (300 MHz, CDCl$_3$): δ=5.71 (s, $^1$H, H-6), 4.78–4.69 (m, $^1$H, H-3); $^{13}$C-NMR (75.5 MHz, CDCl$_3$): δ=202.5, 179.7, 173.4, 164.5, 127.1, 72.4, 55.2, 50.4, 50.2, 45.8, 43.5, 39.9, 38.7, 36.6, 36.1, 29.2, 28.9, 28.4, 25.3, 25.0, 24.2, 23.2, 23.0, 19.3, 17.7, 12.4. (Mass spectroscopy) m/z (FD-MS): 571 [(M+H)$^+$, $C_{36}H_{59}O_5$]

(14) Methylation of oxLig-1

To a solution of purified or synthesized oxLig-1 (7.5 mg, 0.0131 mmol) in ether (2 mL), a diazomethane-ether solution was added at room temperature, and the mixture was stirred for 2 hours. Acetic acid was added to the solution while stirring. One day after addition of acetic acid, the solvent was evaporated to give methylated oxLig-1 preparation.

Hereinafter, a methylated species may be represented with a prefix "Me-."

(15) Analysis Results of Methylated Synthesized oxLig-1

(NMR); $^1$H-NMR (300 MHz, CDCl$_3$): d=5.71 (s, $^1$H, H-6), 4.78–4.69 (m, m, $^1$H, H-3), 3.67 (s, $^1$H, COOCH3); $^{13}$C-NMR (75.5 MHz, CDCl$_3$): d=202.4, 174.7, 173.4, 164.4, 127.1, 72.4, 55.2, 50.4, 45.8, 43.5, 39.9, 38.7, 36.6, 36.4, 36.1, 29.3, 28.4, 26.7, 25.3, 24.2, 23.2, 23.0, 21.6, 19.3, 17.7, 12.4. (Mass spectroscopy) m/z (FD-MS): 585 [(M+H)$^+$, $C_{37}H_{51}O_5$]

(16) Methylation of oxLig-1

Under cooling with ice, 1-methyl-3-nitro-1-nitrosomethylguanidine (0.20 g) was added to a mixture of 2M sodium hydroxide (10 mL) and diethyl ether (10 mL). The resultant mixture was stirred for several minutes, whereby a pale-yellow liquid was separated as an upper layer. The thus-separated liquid was employed for methylation. A diazomethane solution (2 mL) was added dropwise to a solution (1 mL) of a lipid ligand (oxLig-2 or 13-COOH-7KC) (1.0 mg) in diethyl ether at 0° C. Each of the formed two liquids was stored overnight in a refrigerator. TLC analysis revealed that each starting substance was completely converted. The solvent of each solution was removed through air blow, to thereby yield a methyl ester of each ligand as a white, amorphous matter.

(17) Synthesis of 13-COOH-7KC

WSC (95.8 mg, 50 mmol) and DMAP (30.5 mg, 0.25 mmol) were added to an acetone solution (4 mL) containing 7-ketocholesterol (5-cholesten-3β-ol-7-one) (50.1 mg, 0.13 mmol) and tridecanedioic acid (brassylic acid) (61.8 mg, 0.25 mmol). The mixture was stirred at room temperature for two days, and the reaction mixture was concentrated and extracted with chloroform. The extract was sequentially washed with 2M hydrochloric acid, an aqueous saturated sodium hydrogencarbonate solution, and brine. The thus-obtained liquid was dried over magnesium sulfate anhydrate, and the solvent was evaporated. The residue was applied to silica gel chromatography using toluene/ethyl acetate (3:1, v/v), to thereby yield 44 mg of 13-COOH-7KC (yield: 56.0%). NMR spectra and a mass spectrum (FD-MS) of the product were recorded in the same manner as described above.

(NMR); $^1$H-NMR (300 MHz, CDCl$_3$): δ=5.69 (s, $^1$H, H-6), 4.80–4.67 (m, $^1$H, H-3); $^{13}$C-NMR (75.5 MHz, CDCl$_3$): δ=202.2, 179.6, 173.1, 164.7, 126.9, 72.3, 55.3, 50.5, 50.1, 45.3, 43.5, 40.6, 39.2, 38.6, 36.5, 36.0, 29.1, 28.8, 28.3, 25.2, 24.9, 24.1, 23.1, 22.9, 19.2, 17.6, 12.3 (Mass spectroscopy) m/z (FD-MS): 627 [(M+H)$^+$, $C_{40}H_{67}O_5$]

(18) Preparation of Liposomes

Liposomes were prepared through a method as described in [42], with the following lipid compositions. Lipid pro portions by mol of 0, 10, 25, and 50% PS-liposomes are as follows.

DOPC/DPPS/[$^3$H]-DPPC (80 Ci/mmol)
0%: 100/0/0.00225
10%: 90/10/0.00225
25%: 75/25/0.00225
50%: 50/50/0.00225

Lipid proportions by mol of 0, 5, 12.5, and 25% PS-Chol-liposomes are as follows.

DOPC/DPPS/Chol/ [$^3$H]-DPPC (80 Ci/mmol)
0%: 50/0/50/0.00225
5%: 45/5/50/0.00225
12.5%: 37.5/12.5/50/0.00225
25%: 25/25/50/0.00225

Lipid proportions by mol of 0, 10, 20, and 40% oxLig-1 (purified product)-liposomes are as follows.

DOPC/oxLig-1/[$^3$H]-DPPC (80 Ci/mmol)
5%: 100/0/0.00225
10%: 90/10/0.00225
20%: 80/20/0.00225
40%: 60/40/0.00225)

Lipid proportions by mol of 0, 5, 10, 20, 30, and 40% oxLig-1 (purified product)-Chol-liposomes are as follows.

DOPC/Chol/oxLig-1/[$^3$H]-DPPC (80 Ci/mmol)
50%: 50/50/0/0/0.00225
5%: 50/45/5/0.00225
10%: 50/40/10/0.00225
20%: 50/30/20/0.00225
30%: 50/20/30/0.00225
40%: 50/10/40/0.00225 oxLig-1 (synthesized product)-Liposomes were prepared using synthesized oxLig-1 in a manner similar to preparation of oxLig-1 (purified product)-liposomes. A mixture of the desired lipids in chloroform/methanol (1:1, v/v) was placed in a pare-shaped flask and the solvent was removed in a rotary evaporator under reduced pressure. The dried lipids were dispersed with a mixer in 0.3M glucose solution. Then the liposome solution was sonicated for 5 minutes at 70° C. with a probe-type sonicator.

Liposomes of oxLig-2, 13-COOH-7KC, etc. were also prepared in a similar manner by use of the following lipid compositions. Liposomes containing each ligand in an amount of 0, 10, 25, 30, and 50% were prepared by use of a DOPC/ligand/[$^3$H]-DPPC (80 Ci/mmol). The amount of [$^3$H]-DPPC used was 0.225%. As the ligands, cholesteryl linoleate, DPPS, oxLig-1, oxLig-2, methylated oxLig-2 (Me-oxLig-2), 13-COOH-7KC, and methylated 13COOH-7KC (Me-13COOH-7KC) were used.

(19) Cell Culture and Liposome Binding

A monolayer culture of murine macrophage-like cells (J774A.1) obtained from Riken Cell Bank (Tsukuba) was maintained in RPMI 1640 medium supplemented with 10% fetal carf serum (FCS). For binding experiments, the cells (8×10$^5$ cells/mL, RPMI1640) were dispensed in an amount of 1 mL/well into a 12-well culture plate (Sumitomo Bakelite Co., Ltd.) and were incubated for 24 hours at 37° C., then the culture broth was replaced with Celgrosser-P medium (Sumitomo Pharmaceutical Co.). After one hour of preincubation at 37° C., 50 μL of liposomes (50 nmol lipid/well) with or without β$_2$-GPI (200 μg/mL) and WB-CAL-1 (100 μg/mL) were added to each culture, and the cells were incubated at 4° C. and/or 37° C. The wells were next washed with chilled PBS, and the cells were lysed by adding 1 mL of 0.1N NaOH. An aliquot was taken for determination of cellular proteins and of radioactivity associated with the cells. Protein concentration was determined in a manner as described above.

(20) Anti-$\beta_2$-GPI ELISA (ELISA of IgG Autoantibody Against $\beta_2$-GPI)

Anti-$\beta_2$-GPI ELISA (ELISA of IgG autoantibody against $\beta_2$-GPI) was performed through a method as described in [43]. Briefly, $\beta_2$-GPI (10 μg/mL, 50 μL/well) was adsorbed on an oxygenated polystyrene plate (carboxylated, Sumilon C-type, Sumitomo Bakelite Co., Ltd.) by incubating overnight at 4° C. The plates were blocked with 3% gelatin, and 100 μL/well of anti-$\beta_2$-GPI monoclonal antibody or of 100-fold diluted plasma samples was added to the plate, followed by incubation for one hour. A antibody binding to $\beta_2$-GPI was probed using HRP-labeled anti-human IgG or IgM or anti-mouse IgG. The color was developed with $H_2O_2$ and o-phenylenediamine, and OD was measured at 490 nm. Between these steps, extensive washing were done using PBS containing 0.05% Tween 20.

(21) ELISA for Antibodies Against a Protein-oxLig-1 Complex

Synthesized oxLig-1 (50 μg/mL, 50 μL/well) was adsorbed by evaporation on a polystyrene plate (Immulon 1B; Dynex Technologies Inc.), and the plate was then blocked with 1% BSA. Serum samples (diluted 1:100 with PBS containing 0.3% BSA) were incubated in the wells with $\beta_2$-GPI (15 μg/mL) or other proteins for one hour at room temperature. Antibody binding was detected with HRP-labeled anti-human IgG. Further steps were performed through a method as described in "anti-$\beta_2$-GPI ELISA."

(22) $\beta_2$-GPI-Dependent aCL

CL (50 μg/mL, 50 μL/well) was adsorbed on a polystyrene plate (Immulon 1B), and further steps were performed through a method as described in "ELISA for antibodies against a protein-oxLig-1 complex."

(23) Statistical Analysis

Statistical analysis was performed by use of StatView software (product of Abacus Concepts). Comparative studies between the autoantibody and the clinical episode were carried out by means of the Fisher's exact test.

The relationship between the antibody value and the clinical episode was evaluated by means of the Mann-Whitney U-test.

<2> Results (1) Molecular Interaction oxLDL but not native LDL showed highly specific binding to $\beta_2$-GPI (FIG. 1A). A dose-dependent binding of oxLDL to solid phase WB-CAL-1 was observed only in the presence of $\beta_2$-GPI (10 μg/mL), and no specific binding of native LDL was observed (FIG. 1B). In a control experiment, CL showed large extent of binding, while DOPE did not show any specific binding (FIG. 1C). CL also showed dose-dependent binding to WB-CAL-1 in the presence of $\beta_2$-GPI, while DOPE did not (FIG. 1D).

(2) Binding of $\beta_2$-GPI and Anti-$\beta_2$-GPI Antibody to Solid Phase LDLs or Lipids Derived therefrom $\beta_2$-GPI specifically bound with high avidity to immobilized oxLDL, but minimally to native LDL (FIG. 2A). Lipids were extracted from LDLs, immobilized on a plate, and subjected to binding assays for $\beta_2$-GPI by detecting with Cof-22 monoclonal antibody and anti-$\beta_2$-GPI antibodies (i.e., WB-CAL-1 and EY2C9). The assays showed specific binding of $\beta_2$-GPI (FIG. 2B) and of $\beta_2$-GPI-mediated antibody to the lipids derived from oxLDL (FIGS. 2C and 2D), but did not to those derived from native LDL (FIGS. 2B–2D).

(3) Purification and Characterization of a $\beta_2$-GPI-Specific Ligand

The lipids extracted from each LDL were spotted on a TLC plate and developed in solvent A (FIGS. 3A and 3B). In the plates treated with $I_2$ vapor and molybdenum blue, decreased PC (phosphatidylcholine) and increased polar forms co-migrating with lysoPC were observed in lipids derived from oxLDL as compared with derived from of native LDL. By staining with orcin/sulfuric acid, pseudo-positive bands were observed at similar Rf positions of Chol, PC, and CL, and others. In Lieberman-Burchard reaction, a Chol band was observed for both extracts at almost top, and few bands near the Rf position of CL were observed for lipid derived from oxLDL. To identify $\beta_2$-GPI-specific ligands, the developed plates were subjected to ligand blot in which the plates were treated with $\beta_2$-GPI and anti-$\beta_2$-GPI antibodies (FIG. 3B). With all three tested anti-$\beta_2$-GPI antibodies (Cof-22, WB-CAL-1, and EY2C9), two predominant bands and several bands of diffused lipids were stained and observed at similar Rf positions of CL and glycolipids such as galactosylceramide (Gal-Cer) and glucosylceramide (Glc-Cer). The bands detected in the ligand blot were not stained with a spray of molybdenum blue (FIGS. 3A and 3B).

Figure 3:
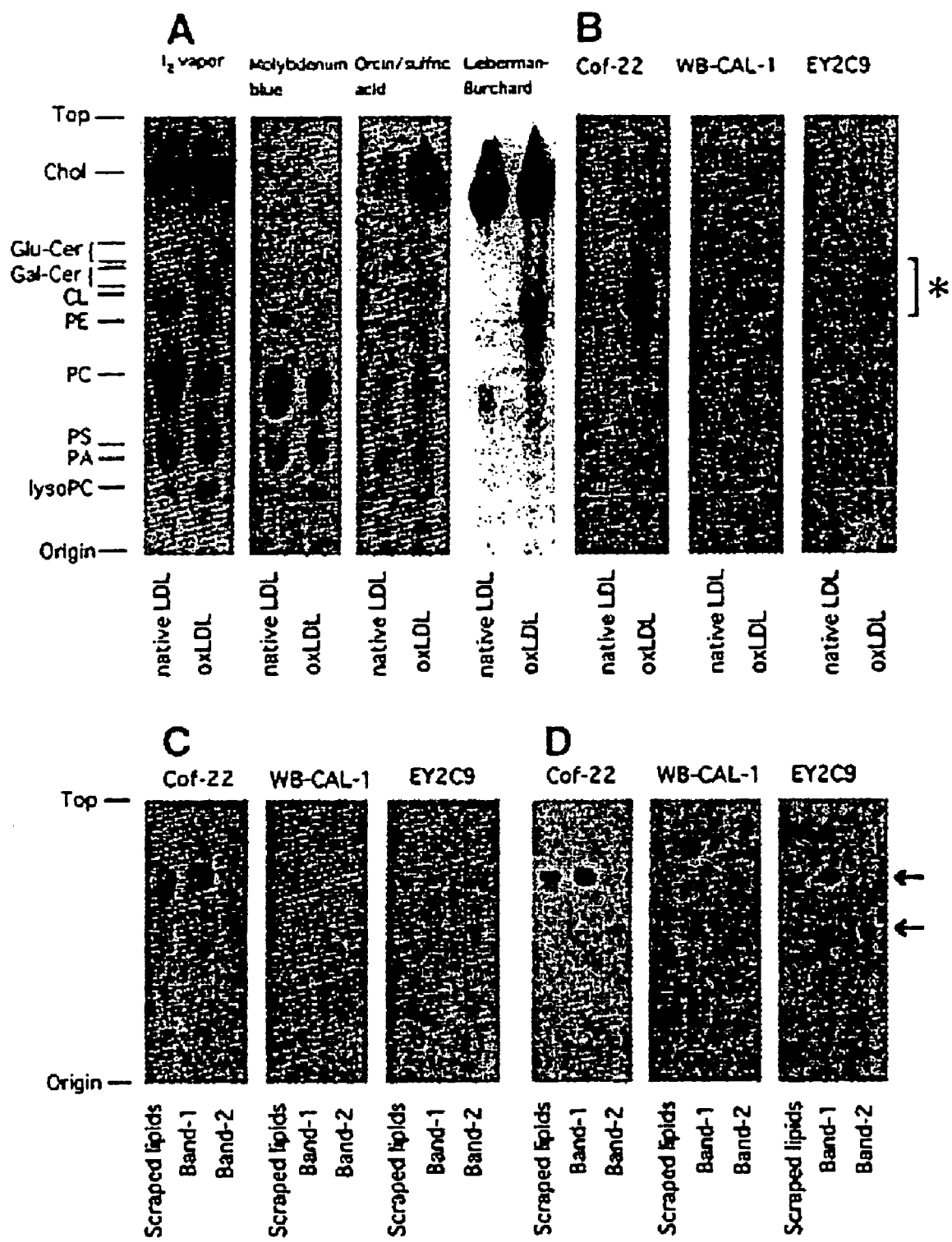
FIG. 3. Thin-layer chromatography (TLC) and ligand blot of lipid extracts from LDLs.
Lipids extracted from LDLs were spotted on silica gel plates and developed in solvent A.
A: Staining with $I_2$ vapor, molybdenum blue, orcin/sulfuric acid, and sulfuric acid/acetic acid as indicated in the figure.
B: Ligand blot was performed with $\beta_2$-GPI and anti-$\beta_2$-GPI antibodies. The region marked with an asterisk was scraped off and subjected to further purification. Glu-Cer represents glucosylceramide, and Gal-Cer represents galactosylceramide.
C: Ligand blot of the scraped lipids (Band-1 and Band-2) was performed by sequential treatment with $\beta_2$-GPI and anti-$\beta_2$-GPI antibodies (2-step)
D: Ligand blot of the eluate was performed by co-incubation of $\beta_2$-GPI and anti-$\beta_2$-GPI antibodies (1-step).

$\beta_2$-GPI-ligand-enriched lipids were scraped from the first TLC plate (hereinafter referred to as "scraped lipids") (FIG. 3B) and were subjected to another TLC (developing in solvent B), and the two major bands were scraped off and subjected to the ligand blot (FIGS. 3C and 3D). Two major bands (indicated by arrows in FIG. 3) reacting with $\beta_2$-GPI were named Band-1 (the upper band) and Band-2 (the lower band).

Band-1 was rarely stained in the sequential treatment with $\beta_2$-GPI and EY2C9 (or WB-CAL-1) (2-step), but was strongly stained in the case of the simultaneous treatment (1-step). In contrast, Band-2 was stained well in either treatment with $\beta_2$-GPI and EY2C9 (Densitometric analysis in individual experiments indicated significant difference).

Figure 4:
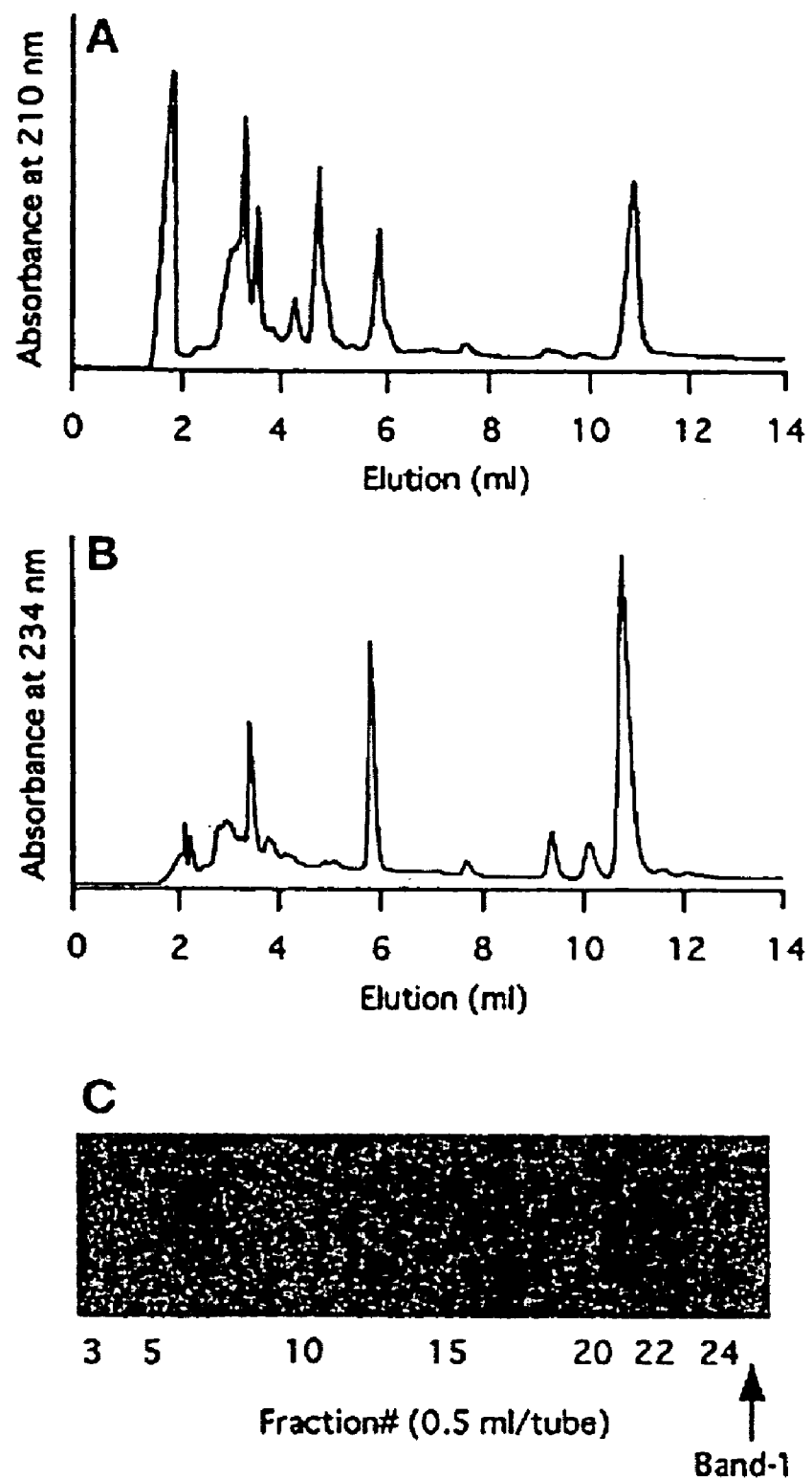
FIG. 4. Elution profiles of Band-1 by reversed phase high performance liquid chromatography (HPLC).

The alkaline hydrolyzed (20% NaOH, 100° C., 30 minutes) product of Band-1 did not bind to $\beta_2$-GPI in the ligand blot (data not shown). Band-1 was subjected to reversed phase HPLC by use of solvent C. A major peak appeared at 22 min that positively stained in the ligand blot with $\beta_2$-GPI and EY2C9 (FIG. 4), and was attributable to very weak Lieberman-Burchard reaction. This peak was designated as oxLig-1. From 100 mg protein equivalent of oxLDL, approximately 2.5 mg of oxLig-1 was recovered.

(4) Purification of oxLig-2

The oxLig-2, which is a specific ligand to $\beta_2$-GPI, was purified from a ligand-containing fraction through reverse phase HPLC by use of a Sephasil Peptide C18 column (4.6 mm×250 mm, product of Amersham-Pharmacia Biotech). The thus-separated Band-2 was eluted at a flow rate of 0.5 mL/min by 0.2% acetic acid-containing water (solvent E) and acetonitrile/isopropanol (30/70, v/v) (solvent D) with linear gradation (50–100%) in concentration for 15 minutes and then by 100% solvent D for 15 minutes. The absorbance (A) at 210 nm or at 234 nm was monitored. The eluate was fractionated (1 mL/tube) every two minutes. Each fraction was applied to a TLC plate and subjected to ligand blot analysis using $\beta_2$-GPI and EY2C9.

(5) Purification and Properties of oxLig-2

Through HPLC of Band-2, a novel ligand (oxLig-2) was obtained (FIGS. 16A and 16B).

The peaks corresponding to specific binding to $\beta_2$-GPI and EY2C9 were observed at about 26.7 min (equivalent to elution volume of 13.4 mL). In order to confirm the purification degree of oxLig-2 (fraction 14), the fraction was subjected to HPLC again under the same conditions (FIGS. 16C and 16D), and to an LC/MS analysis.

In a positive ionization mass spectrum of oxLig-2, three signals (m/z: 383, 441, and 627) were detected (FIG. 17C).

no such binding was observed with respect to solid-phase methylated oxLig-2, methylated 13-COOH-7KC, or control lipid (cholesteryl linoleate). Similar results were obtained in the case where a mouse monoclonal anti-$\beta_2$-GPI antibody obtained from mice immunized with human $\beta_2$-GPI was used (Table 1). These three antibodies did not bind to the immobilized cholesterol or to 7-ketocholesterol. From these results and previously reported results [52], it is concluded that the structure of oxLig-2 is highly likely to be an oxide of cholesteryl linoleate, 4,12-dioxo-12-(7-ketocholest-5-en-3$\beta$-yloxy)dodecanoic acid (FIG. 18).

TABLE 1

| Solid-phase lipid | $\beta$2-GPI binding (Cof-22 binding) | | WB-CAL-1 binding | | EY2C9 binding | |
|---|---|---|---|---|---|---|
| (Ligand) | No treatment | Methylation | No treatment | Methylation | No treatment | Methylation |
| Cholesteryl linoleate | 0.061 +/− 0.005 | N.T. | 0.056 +/− 0.002 | N.T. | 0.074 +/− 0.012 | N.T. |
| oxLig-1 | 1.307 +/− 0.105 | N.T. | 0.945 +/− 0.068 | N.T. | 1.458 +/− 0.062 | N.T. |
| oxLig-2 | 1.002 +/− 0.084 | 0.204 +/− 0.029 | 0.518 +/− 0.023 | 0.106 +/− 0.018 | 1.018 +/− 0.121 | 0.076 +/− 0.018 |
| 13-COOH-7KC | 1.303 +/− 0.049 | 0.094 +/− 0.002 | 0.336 +/− 0.027 | 0.077 +/− 0.002 | 1.062 +/− 0.040 | 0.052 +/− 0.000 |

(Means ± SD (n = 3) of the absorbance at 490 nm, N.T.: not measured)

Two small peaks; i.e., m/z of 383 (attributable to 7-ketocholesterol) and of 441 (attributable to 7-ketocholesterol (+acetone)) are similar to those observed in the case of ox-Lig-1 and 13-COOH-7-KC (FIGS. 17A, 17C, and 17E).

The signals of 571, 627, and 627 (m/z) shown in the positive ionization mass spectra of oxLig-1, oxLig-2, and 13-COOH-7KC, respectively, were identified as respective parent ions [M+H]+ (FIGS. 17A, 17C, and 17E). The signals of 569, 625, and 625 (m/z) shown in the negative ionization mass spectra of oxLig-1, oxLig-2, and 13-COOH-7KC, respectively, were identified as respective parent ions [M+H]− (FIGS. 17B, 17D, and 17F). In the spectrum of oxLig-2, a signal of 627 (m/z) was identified as a parent ion of dihydro-oxLig-2 (FIG. 17D). In the negative mode, the signals of 187, 243, and 243 (m/z) shown in the spectra of oxLig-1, oxLig-2, and 13-COOH-7KC, respectively, were identified as respective fragment ions [D–H]− (FIGS. 17B, 17D, and 17F, and FIG. 18).

In all TLC ligand blot analyses using solvent A or B, the Rf position with respect to oxLig-2 is lower than that of the relevant monocarbonyl derivatives (oxLig-1 and 13-COOH-7KC). The feature coincides with the presumed difference in polarity (FIGS. 3, 8, and 15).

In the TLC ligand blot analysis using solvent B, the Rf positions in the bands with respect to oxLig-2 and 13-COOH-7KC methylated by diazomethane (Me-oxLig-2 and Me-13-COOH-7KC, respectively) were higher than that of the relevant unmethylated ligands (FIGS. 8 and 15). The peak corresponding to oxLig-2 (26.7 min) in reverse phase HPLC was observed earlier than oxLig-1 (27.3 min) and 13-COOH-7KC (28.9 min). The peaks corresponding to methylated oxLig-2 and methylated 13-COOH-7KC were observed (27.1 min and 30.0 min, respectively) later than those of the unmethylated species. Surprisingly, in TLC ligand blot analyses, the interaction of $\beta_2$-GPI and the anti-$\beta_2$-GPI antibodies (Cof-22 and EY2C9) with each ligand was completely suppressed through ligand methylation.

In ELISA of the anti-$\beta_2$-GPI antibodies by use of a ligand-coated plate, significant binding of the anti-$\beta_2$-GPI autoantibodies (WB-CAL-1 and EY2C9) to solid-phase oxLig-1, oxLig-2, and 13-COOH-7KC were observed, but FIG. 15 shows the results of ligand blot with respect to oxLig-2, Me-oxLig-2, 13-COOH-7KC, and Me-13-COOH-7KC. As is clear from FIG. 15, reactivity of $\beta_2$-GPI and that of the $\beta_2$-GPI antibody is lost through methylation of oxLig-2 and 13-COOH-7KC.

oxLig-1 was further analyzed through LC/MS. The intensities of both positive and negative ions attributed to oxLig-1 were detected for the main peak (at 8.3 min) at 234 nm (FIG. 5A). A positive ionization mass spectrum gave a signal at m/z 571, which was considered to be attributed to (M+H)+, and at m/z 383 (FIG. 5D), which was identical to that attributed to ionized 7-ketocholesterol (FIG. 5B).

In the negative ion mode, a signal of fragment ion was detected at m/z 187 (FIG. 5C). oxLig-1 was treated with diazomethane in diethyl ether to give methylated oxLig-1, which was analyzed through LC/MS. Methylated oxLig-1 was eluted later than oxLig-1 (FIG. 5A, lower), and signals of the largest fragment ion (9.0 min) was detected at m/z 585 and at m/z 201, in the positive and negative ion modes, respectively (FIGS. 5E and 5F). These data are consistent with the structure of 9-oxo-9-(7-ketocholest-5-en-3$\beta$-yloxy) nonanoic acid.

(6) Synthesis and Analysis of oxLig-1

In order to confirm the structure of oxLig-1, oxLig-1 was synthesized from 7-ketocholesterol and azelaic acid. As shown in FIG. 6, the materials were processed with WSC and DMAP in acetone at room temperature for two days, whereby both materials were conjugated each other. The product was isolated through column chromatography on silica gel. The structure of the synthesized oxLig-1 was verified to purified oxLig-1 through $^1$H- and $^{13}$C-NMR spectroscopy and FD mass spectrometry. In the $^1$H-NMR spectrum of synthesized oxLig-1 (synthesized oxLig-1) (FIG. 7A), the signals of H-3 and H-6 are shown at $\delta$ 4.69–4.78 and 5.71 ppm as multiplet and singlet, respectively. Furthermore, three peaks assignable to carbonyl carbons are shown at $\delta$ 202.5, 179.7, and 173.4 ppm together with two signals of olefin carbons at $\delta$ 164.5 and 127.1 ppm (FIG. 7B).

The synthesized oxLig-1 was then esterified with diazomethane in diethyl ether to give methylated oxLig-1. In FIGS. 7C and 7D, by $^1$H- and $^{13}$C-NMR spectra of synthesized oxLig-1 are shown. The new singlet was observed in its $^1$H-NMR spectrum at δ 3.67 ppm, strongly suggesting that oxLig-1 has a carboxyl group (FIG. 7C). Then, synthesized oxLig-1 was subjected to TLC and ligand blot analysis with $β_2$-GPI and anti-$β_2$-GPI antibodies. Synthesized oxLig-1 showed the same Rf position and binding characteristics to Cof-22, WB-CAL-1, and EY2C9 antibodies, as previously described for oxLig-1 derived from oxLDL (FIGS. 3 and 8).

The synthesized oxLig-1 and its methylated compound were further analyzed through LC/MS. The LC chromatograms and mass spectra of both compounds (FIG. 9) were identical to the corresponding compounds derived from oxLDL (FIG. 5). In FIG. 9D, the small peak at 8.3 min is attributed to synthesized oxLig-1 that remained underivatized after the methylation reaction. The underivatized material was identified as synthesized oxLig-1 through mass spectrometry.

(7) Liposome Binding to Macrophages

Binding to the J774A.1 cells of exogenous PS-Chol-liposomes increased depending on the amount of DPPS (FIG. 10). In contrast, binding to the cells of oxLig-1-Chol-liposomes was relatively low. Similar binding profiles were obtained with Chol-free liposomes of PS or oxLig-1. When mouse peritoneal macrophages were used in place of J774A.1 cells, comparable liposome binding was observed.

(8) Antibody-Dependent Liposome Binding to Macrophages

Binding (4° C., 2 hours) of PS-liposomes to oxLig-1-liposomes increased dramatically upon simultaneous addition of $β_2$-GPI and WB-CAL-1, and was also dependent on the concentration of WB-CAL-1 (FIGS. 11A and 11B). In the same assay, subclass-matched control antibodies had no effect on such binding. The uptake (37° C., 5 hours) of oxLig-1-liposomes by J774A.1 cells increased significantly by incubating (4.36 pmol [$^3$H]DPPC/mg protein) with $β_2$-GPI and WB-CAL-1, as compared to incubation without $β_2$-GPI and WB-CAL-1 (0.72 pmol [$^3$H]DPPC/mg protein) (data not shown). As shown in FIG. 11C, binding of synthesized oxLig-1-liposomes to the macrophages also increased depending on the ligand concentration in liposomes. In the case of synthesized oxLig-1, the binding reached almost plateau at the concentration of 10 mL %.

(9) Binding of Liposomes Containing oxLig-2, 13-COOH-7KC, or the Like to Macrophage Direct binding of liposomes containing oxLig-1, oxLig-2, or 13-COOH-7KC to macrophages, J774A.1 cells, was compared with that of liposomes containing DPPS. DPPS-containing liposomes exhibited binding to the macrophages with ligand concentration dependency. In contrast, binding of liposomes containing oxLig-1, oxLig-2, or 13-COOH-7KC to macrophages was relatively low or negligible small (FIG. 19). As is clear from FIG. 19, scavenger receptors are not related to binding of these liposomes to macrophages except the case of DPPS-containing liposomes. In other words, uptake of liposomes containing oxLig-1, oxLig-2, or 13-COOH-7KC to J774A.1 cells was significantly enhanced in the presence of both $β_2$-GPI and an anti-$β_2$-GPI antibody (WB-CAL-1), as compared with cholesteryl linoleate-liposomes (control) (FIGS. 20A, 20B, 20C, and 20D). In contrast, substantially no binding of liposomes was observed after methylation of oxLig-2 or 13-COOH-7KC (FIGS. 20C and 20D).

(10) Detection of Autoantibodies in APS Patients with Episodes of Arterial Thrombosis through ELISA Using a $β_2$-GPI-Synthesized oxLig-1 Complex.

As shown in FIG. 12, autoantibodies against a complex of $β_2$-GPI and synthesized oxLig-1 were detected in APS patients at high frequency. There was a good correlation between values of autoantibodies against the complex antigen and those of $β_2$-GPI-dependent aCL or anti-$β_2$-GPI antibodies. So far as the tests were preformed, such autoantibodies derived from APS cross-reacted with $β_2$-GPI complexed with CL or oxLig-1, but not that complexed with oxidized PAPC (oxPAPC) (Table 2, Exp-1). The antibody binding did not correlate with the amount of TBARS in lipid. Further, the antibody binding was provided only by the interaction between oxLig-1 and intact $β_2$-GPI (Exp-2). In contrast, no antibody binding was provided by nicked $β_2$-GPI or haptoglobin having "sushi domains" (which did not have PL binding property).

TABLE 2

| Experiment 1 Solid-phase lipid | Binding of $β_2$-GPI-dependent aCL (Absorbance, mean ± SD, n = 3) | | | | |
| --- | --- | --- | --- | --- | --- |
| (TBARS)[a] | Cof-22 | EY2C9 | WB-CAL-1 | APS-1[b] | APS-2[b] |
| CL (4.46) | 1.132 ± 0.025 | 1.269 ± 0.014 | 1.361 ± 0.008 | 2.099 ± 0.216 | 1.282 ± 0.041 |
| Synthesized oxLig-1 (0.66) | 1.066 ± 0.114 | 0.915 ± 0.072 | 1.035 ± 0.062 | 1.130 ± 0.177 | 1.222 ± 0.057 |
| PAPC (107.8) | 0.019 ± 0.003 | 0.011 ± 0.003 | 0.012 ± 0.001 | 0.000 ± 0.001 | 0.010 ± 0.002 |
| oxPAPC[c] (218.3) | 0.073 ± 0.007 | 0.009 ± 0.002 | 0.015 ± 0.005 | 0.007 ± 0.002 | 0.015 ± 0.001 |
| Experiment 2 | Binding of protein-dependent oxLig-1 antibody (Absorbance, mean ± SD, n = 3) | | | | |
| Added protein | Cof-22 | EY2C9 | WB-CAL-1 | APS-1[b] | APS-2[b] |
| w/o | 0.050 ± 0.002 | 0.005 ± 0.001 | 0.005 ± 0.002 | 0.012 ± 0.003 | 0.014 ± 0.001 |
| $β_2$-GPI | 1.007 ± 0.031 | 1.147 ± 0.028 | 0.812 ± 0.023 | 1.043 ± 0.054 | 0.755 ± 0.024 |
| Nicked $β_2$-GPI | 0.164 ± 0.007 | 0.005 ± 0.001 | 0.003 ± 0.001 | 0.008 ± 0.003 | 0.011 ± 0.001 |
| Haptoglobin | 0.049 ± 0.001 | 0.006 ± 0.001 | 0.006 ± 0.001 | 0.018 ± 0.011 | 0.015 ± 0.002 |
| Ovalbumin | 0.042 ± 0.001 | 0.004 ± 0.002 | 0.006 ± 0.002 | 0.009 ± 0.004 | 0.016 ± 0.001 |

Table 2 shows the results of binding of anti-$\beta_2$-GPI antiphospholipid antibodies (Abs) to lipid-proptein complexes observed through enzyme-linked immunosorbent assay (ELISA).

Data shown in Experiment 1 represent binding of antibodies in the presence of $\beta_2$-GPI (15 μg/mL), and data shown in Experiment 2 represent the results of ELISA performed by use of a synthesized oxLig-1-solidified plate in the presence of each of the proteins (15 μg/mL) shown in Table 2. The amount of TBARS (thiobarbituric acid reactive substance) shown in the Table is based on nmol (malondialdehyde equivalent)/mg (lipid). APS-1 and APS-2 were obtained from serum samples of APS patients having an episode of arterial thrombosis with removal of $\beta_2$-GPI. oxPAPC was obtained by exposing PAPC in air at room temperature for 24 hours. Nicked $\beta_2$-GPI was prepared through plasmin treatment. [43].

(11) The Following Results were Obtained through Further Analysis of the Relationship Between the anti-$\beta_2$-GPI-ox-Lig-1 Antibody Value and Clinical Observations.

When the antibody value (OD) of a plasma sample exceeded the averaged (30 healthy volunteers) antibody value by more than 3×SD (standard deviation), the sample was regarded to be positive to a specific antibody (as a cut-off value).

The IgG anti-$\beta_2$-GPI-oxLig-1 antibody was observed in 73% the initial-stage APS patients (35/48); in 59% the APS patients with SLE (second-stage APS) (23/39); and in 11% the solo-SLE patients (5/46) (Table 3).

TABLE 3

| Patient | No. | % |
| --- | --- | --- |
| SLE only | 46 | |
| APS | 87 | |
| Primary | 48 | 55 |
| Secondary | 39 | 45 |
| Clinical profile | | |
| Thrombosis | 75 | 56 |
| Arterial thrombosis only | 27 | 20 |
| Venous thrombosis only | 29 | 22 |
| Arterial and venous thrombosis | 19 | 14 |
| Pregnancy morbidity | 32/120 | 27 |
| Thrombocytopenia | 24/128 | 19 |
| Autoantibody | | |
| $\beta_2$-GPI-dependent aCL (anti-$\beta_2$-GPI-CL antibody) | 77/133 | 58 |
| Anti-$\beta_2$-GPI antibody | 48/133 | 36 |

TABLE 3-continued

| Patient | No. | % |
| --- | --- | --- |
| Anti-$\beta_2$-GPI-oxLig-1 antibody | 63/133 | 47 |
| Lupus anticoagulants | 62/113 | 55 |

In all patients (133 patients) investigated in the present example, the anti-$\beta_2$-GPI-oxLig-1 antibody value was found to be strongly correlated with the antibody value of the $\beta_2$-GPI-dependent aCL (anti-$\beta_2$-GPI-CL antibody) and that of the anti-$\beta_2$-GPI antibody (correlation factor $r^2$: 0.72 and 0.81, respectively) (FIG. 14).

In these patients (133 APS and/or SLE patients), significant relationship was observed between the anti-$\beta_2$-GPI-oxLig-1 antibody value and episodes of thrombosis (arterial and/or venous thrombosis, arterial thrombosis, and venous thrombosis) or pregnancy morbidity, but no significant relationship was observed between the antibody value and thrombocytopenia ($p=4.2\times10^{-8}$ (Fisher's exact test); Odds ratio 8.15, $p=1.7\times10^{-7}$; 8.00, $p=0.018$; 2.29, $P=0.0077$; 3.03, and $P=0.31$; 1.38, respectively) (Table 4). Assay sensitivity, specificity, and expected values with respect to arterial thrombosis diagnosis were remarkably excellent as compared with diagnosis of venous thrombosis, pregnancy morbidity, and thrombocytopenia (Table 4).

TABLE 4

| Auto-antibody | Thrombosis | | | | Arterial thrombosis | | | | Venous thrombosis | | | | Pregnancy morbidity | | | | Thrombocytopenia | | | |
| --- | --- | --- | --- | --- | --- | --- | --- | --- | --- | --- | --- | --- | --- | --- | --- | --- | --- | --- | --- | --- |
| | + | − | p* | Odds ratio | + | − | p* | Odds ratio | + | − | p* | Odds ratio | + | − | p* | Odds ratio | + | − | p* | Odds ratio |
| Positive | 51 | 12 | $4.2\times10^{-8}$ | 8.15 | 36 | 27 | $1.7\times10^{-7}$ | 8.00 | 29 | 34 | 0.018 | 2.29 | 21 | 34 | 0.0077 | 3.03 | 13 | 48 | 0.31 | 1.38 |
| Negative | 24 | 46 | | | 10 | 60 | | | 19 | 51 | | | 11 | 54 | | | 11 | 56 | (NS) | |
| Specificity | | | 0.79 | | | | 0.69 | | | | 0.60 | | | | 0.61 | | | | 0.54 | |
| Sensitivity | | | 0.68 | | | | 0.78 | | | | 0.60 | | | | 0.63 | | | | 0.54 | |
| Expected Value | | | 0.73 | | | | 0.72 | | | | 0.60 | | | | 0.63 | | | | 0.54 | |

+: Presence
−: Absence
p*: Fisher exact test,
NS: No significant difference

In addition, as compared with the antibody value of the $\beta_2$-GPI-dependent aCL and that of the anti-$\beta_2$-GPI antibody, the anti-$\beta_2$-GPI-oxLig-1 antibody value was more strongly correlated with thrombosis (arterial and/or venous thrombosis) ($p=1.5\times10^{-6}$ (Fisher's exact test); Odds ratio 6.02, $p=5.2\times10^{-5}$; 4.93, respectively).

The anti-$\beta_2$-GPI-oxLig-1 antibody values of the patients having an episode of thrombosis (arterial and/or venous thrombosis, arterial thrombosis, or venous thrombosis) or a pregnancy-related disease was significantly higher than that of subjects having no such an episode (Mann-Whitney U-test, $p<0.0001$, $p<0.0001$, $P=0.025$, and $P=0.011$) (FIG. 15). In contrast, no relationship was observed between the presence of the antibody or the antibody value and the episode of thrombocytopenia (Mann-Whitney U-test, $p=0.45$).

<3> Discussion

A strong evidence for specific binding interactions among $\beta_2$-GPI, oxLDL, and an anti-$\beta_2$-GPI autoantibody, was obtained by use of an optical biosensor. A ligand specific to $\beta_2$-GPI was purified, and its structure and involvement in macrophage uptake of oxLDL was characterized by using a synthesized ligand. The structure of the ligand was confirmed by reproducing its properties with chemically synthesized 9-oxo-9-(7-ketocholest-5-en-3β-yloxy)nonanoic acid.

It appears that oxidation of LDL plays an important role in atherogenesis [44]. To examine mechanisms related to the development of atherosclerosis, several experimental models of denatured LDL, such as MDA-LDL, acetylated LDL, and $CuSO_4$-mediated oxLDL ($CuSO_4$-oxLDL), have been used. Among these LDLs, $Cu^{2+}$-ion can induce LDL oxidation, resulting in highly reproducible LDL damage [45]. This process leads to production of oxLDL that shares many structural and functional properties with LDL oxidized by cells or LDL extracted from arterial atherosclerotic plaques. Incubation of LDL with several different types of cells or incubation of LDL with $Cu^{2+}$-ion even in the absence of cells result in generating oxidatively modified LDL with similar properties [46]. There is general agreement about the use of $CuSO_4$-oxLDL as an autoantigen because oxLDL has been found in atheromatous lesions and oxLDL extracted from atherosclerotic lesions exhibits nearly all of the physicochemical and immunological properties of $CuSO_4$-oxLDL [24].

Antibodies against oxLDL recognize substances in atherosclerotic lesions that are not present in normal arteries. It has been reported that aCL raised in SLE patients cross-reacted with MDA-LDL [27], while other research groups found that another population of anti-oxLDL antibodies reacted to oxidized PC (such as POVPC)-protein adducts in LDL molecules [33, 47].

However, recent studies elucidated that TBARS generation was not consistent with $β_2$-GPI binding to $CuSO_4$-oxLDL [48].

As MDA is a hydrophilic short-chain aldehyde, it readily diffuses away from LDL particles [49]. It was also observed that, after dialysis, TBARS in the oxLDL preparations decreased to undetectably low levels. In this study, $CuSO_4$-oxLDL showed highly specific binding to immobilized $β_2$-GPI (FIG. 1A). The weak binding of native LDL to $β_2$-GPI might reflect the binding of $β_2$-GPI to lipoprotein [a], which is composed of LDL and apolipoprotein [a] (apo[a]), as described in [50]. However, such interaction between native LDL and $β_2$-GPI may not expose suitable epitopes to anti-$β_2$-GPI autoantibody (FIG. 1B). Further, highly specific binding of anti-$β_2$-GPI autoantibody, two monoclonal antibodies, and antibodies in two typical anti-$β_2$-GPI positive serum samples (derived from APS patients with episodes of arterial thrombosis) was only observed in the presence of the complex of $β_2$-GPI and the lipid ligand derived from $CuSO_4$-oxLDL (FIGS. 2, 3, and 12, Table 2). Oxidative modification of LDL actually includes a series of complex changes such as lipid peroxidation, modification of side chains of amino acids by active aldehydes, increased surface charge, and polymerization.

Among diverse modified molecules in oxLDL, $β_2$-GPI obviously bound to a component in the lipid moiety.

Linoleic acid is a predominant polyunsaturated fatty acid in LDL and is present mainly as Chol-ester [51].

In mildly oxidized LDL, cholesteryl hydroperoxyoctadecadienoate (Chol-HPODE) and cholesteryl hydroxyoctadecadienoate (Chol-HODE) were detected as main constituents of oxidation products [52]. Chol-HPODE has been reported to inactivate platelet-derived growth factor [53]. 7-Hydroxycholesterol (both free and esterified) is the major oxysterol formed in an earlier stage of LDL oxidation, with 7-ketocholesterol dominating at later stages [54]. Recent studies indicated that elevated plasma levels of 7β-hydroxycholesterol may be associated with an increased risk of atherosclerosis [55]. At later stages in LDL oxidation, cholesteryl esters or 7-ketocholesteryl esters of 9-oxononanoate derived from cholesteryl linoleate [56] were detected as the most abundant fraction of oxidized cholesteryl linoleate [57, 58]. Cholesteryl ester core-aldehydes react with the free ε-amino group of lysines, form complexes with proteins, and were evident in human atheroscleorotic lesions [58, 59]. In the present study, oxLig-1 was identified to be 9-oxo-9-(7-ketochlest-5-en-3β-yloxy)nonanoic acid, one of the oxidation products of cholesteryl linoleate, and a major ligand for $β_2$-GPI. However, it still remains to be elucidated whether 9-oxo-9-(7-ketochlest-5-en-3β-yloxy)nonanoic acid is actually present in biological samples as an oxLDL ligand.

Chemically modified LDL can be rapidly taken up by macrophages via receptor-mediated endocytosis, resulting in foam cell formation [44]. As models of oxLDL, oxLig-1- and PS-liposomes were used to study their binding to J774A.1 cells (FIG. 7). PS-liposomes bound to macrophages via scavenger receptor(s), while oxLig-1 did not seem to be a major ligand for scavenger receptors. However, the binding of oxLig-1-liposomes to J774A.1 cells at 4° C. increased up to 14 times when oxLig-1-liposomes were added simultaneously with $β_2$-GPI and WB-CAL-1. The uptake of oxLig-1-liposomes with J774A.1 cells at 37° C. also significantly increased by incubation with $β_2$-GPI and WB-CAL-1. This binding and uptake might be mediated by the Fcγ receptor. The uptake by macrophages of immune complexes containing oxLDL through the Fcγ type I receptor transformed macrophages into foam cells [60, 61], and could accelerate the atherogenic process [62–64].

Autoantibodies against a solid phase oxLig-1 complexed with $β_2$-GPI were detected in serum samples collected from APS patients having episodes of arterial thrombosis (FIG. 12). Further, there was a good correlation between anti-$β_2$-GPI-oxLig-1 antibody value, anti-$β_2$-GPI antibody value, and $β_2$-GPI-dependent aCL titer. In contrast, it has been reported that some aPL recognize adducts of oxidized PLs and $β_2$-GPI [31]. It has not been determined whether oxLig-1 can form covalent adducts with $β_2$-GPI, and the possibility can not yet be excluded. However, it is clear that interaction between oxLig-1 and $β_2$-GPI is essential to express antigenicity for the autoantibodies shown in Table-2, Exp-2. It was also suggested that domain V, which contains the- PL-binding region [15, 16], is distinguished from domains in which epitopes, recognized by aPL in APS patients, locate [38, 65].

In addition to promoting lipid deposition in macrophages, oxLDL is considered to have another characteristic that it may accelerate atherogenesis. oxLDL is chemotactic for monocytes and for T cells [66, 67] and is cytotoxic for cultured endothelial cells [68]. It has been also reported that peroxisome proliferator-activated receptor γ (PPARγ), a transcriptional regulator of genes linked to lipid metabolisms, is activated by components of oxLDL, such as 9-HODE, and 13-HODE and CD36, a scavenger receptor, is up-regulated by a combination of PPARγ and retinoid X receptor ligands [69]. PPARγ enhances the uptake of oxLDL, thereby promoting foam cell formation. It remains to be determined if oxLig-1 has any specific influence on nuclear receptors or other biological functions such as intracellular signal transductions.

In summary, a ligand for $β_2$-GPI present in oxLDL was isolated and characteirzed. The ligand (oxLig-1), i.e., 9-oxo-9-(7-ketochlest-5-en-3β-yloxy)nonanoic acid, mediates liposome uptake by macrophages in the presence of $β_2$-GPI and an anti-$β_2$-GPI autoantibody. These findings on the ligand provide a specific structural and mechanistic link between $\beta_2$-GPI and anti-$\beta_2$-GPI autoantibodies and atherogenesis in APS.

The ω-carboxyl group introduced through oxidation by $Cu^{2+}$ was indicated to play an important role in interaction between $\beta_2$-GPI and the ligand. The ligand, oxLig-2, was identified as 4,12-dioxo-12-(7-ketocholest-5-en-3β-yloxy) dodecanoic acid (FIG. 18).

Although results of methylation of oxLig-2 indicated that the carboxylic group was present in the acyl chain, the accurate position of the ketonic moiety cannot be determined through mass spectroscopy. However, since cholesteryl linoleate is one of the important cholesteryl esters of LDL [52], the positions of the ketonic moieties are highly likely 9-position and/or 13-position.

$\beta_2$-GPI did not bind to cholesterol, 7-ketocholesterol, or cholesteryl linoleate, but did form significant bonding to oxLig-1, oxLig-2, or 13-COOH-7KC. Thus, the formed oxysterol esters having a carboxylated long acyl chain constitute a novel class of amphipathic ligands suitable for $\beta_2$-GPI. Furthermore, the fact that methylation of these ligands inhibits interaction between the ligands and $\beta_2$-GPI indicated requirement of a free carboxylic group for structure recognition.

The results of experiments indicated that oxidized cholesteryl esters, particularly such esters having 7-ketocholesterol and a carboxyl group in the acryl group functioned as ligands to $\beta_2$-GPI and an anti-$\beta_2$-GPI autoantibody. One predominant biologically oxide compound originating from plasma LDL may be a ω-carboxylated oxysterol such as oxLig-1 or oxLig-2. 13-COOH-7KC, which is an artificially synthesized compound, also formed significant bonding to $\beta_2$-GPI, similar to the cases of oxLig-1 and oxLig-2.

<4> Fabrication of the Kits of the Present Invention

The kit 1 of the present invention containing the following elements was prepared:
1. A 96-well immuno-plate on which oxLig-1 has been immobilized (1 sheet);
2. $\beta_2$-GPI standard solution (1 set);
3. Anti-$\beta_2$-GPI antibody (WB-CAL-1) (1 vial);
4. HRP-labeled anti-mouse IgG antibody (1 vial);
5. o-Phenylenediamine solution (1 vial);
6. Aqueous hydrogen peroxide (1 vial); and
7. Reaction-terminating liquid (1N HCl) (1 vial).

The kit 2 of the present invention containing the following elements was prepared:
1. A 96-well immuno-plate on which oxLig-1 has been immobilized (1 sheet);
2. $\beta_2$-GPI (1 vial);
3. HRP-labeled anti-human IgG antibody (1 vial);
4. Tetramethylbenzidine solution (1 vial);
5. Aqueous hydrogen peroxide (1 vial); and
6. Reaction-terminating liquid (1N HCl) (1 vial).

<5> References
15. J. immunol. 152: 653–659
16. EMBO J. 18: 5166–5174
24. J. Clin. Invest. 84: 1086–1095
27. Lancet. 341: 923–925.
31. J. Clin. Invest. 98: 815–825
33. J. Clin. Invest. 103: 117–128
35. J. Immunol. 148: 3885–3891
36. Arthritis Rheum. 37: 1453–1461
37. J. immunol. 149: 1063–1068
38. Blood. 87: 3262–3270
39. J. Clin. Invest. 43: 1345–1353
40. Anal. Biochem. 95: 351–358
41. J. Biol. Chem. 226: 497–509
42. J. Biol. Chem. 265: 5226–5231
43. Int. Immunol. 12: 1183–1192
44. J. Biol. Chem. 272: 20963–20966
45. Clin. Chem. 38: 2066–2072
46. Eur. Heart J. 11 (Suppl. E): 83–87
47. J. Biol. Chem. 269: 15274–15279
48. Lupus. 7 (Suppl. 2): 135–139
49. J. Lipid Res. 28: 495–509
50. Blood. 90: 1482–1489
51. Arterioscler. Thromb. Vasc. Biol. 15: 1131–1138
52. Anal. Biochem. 213: 79–89
53. J. Biol. Chem. 273: 19405–19410
54. J. Lipid Res. 38: 1730–1745
55. Atherosclerosis. 142: 1–28
56. FEBS Lett. 304: 269–272
57. J. Lipid Res. 36: 1876–1886
58. J. Lipid Res. 38: 1347–1360
59. J. Lipid Res. 39: 1508–1519
60. J. Exp. Med. 168: 1041–1059
61. Atherosclerosis. 135: 161–170
62. Arterioscler. Thromb. 12: 1258–1266
63. Arterioscler. Thromb. Vasc. Biol. 15: 990–999
64. J. Lipid Res. 36: 714–724
65. Proc. Natl. Acad. Sci. USA 95: 15542–15546
66. Proc. Natl. Acad. Sci. USA 84: 2995–2998
67. J. Clin. Invest. 92: 1004–1008
68. Atherosclerosis 3: 215–222
69. Cell. 93: 229–240

INDUSTRIAL APPLICABILITY

The derivative of the present invention specifically binds to $\beta_2$-GPI, and thus can be used for, for example, detecting or purifying $\beta_2$-GPI. The derivative can also be applicable to the solid phase of the present invention, the assay method of the present invention, the detection method of the present invention, and the assay kit of the present invention. Thus, the derivative of the present invention is remarkably useful. Furthermore, oxLDL can be assayed making use of the derivative of the present invention through a competitive method and the derivative can be employed as a standard substance for oxLDL assay.

The solid phase of the present invention can be used, for example, in simple, quick detection of $\beta_2$-GPI or purification of $\beta_2$-GPI as well as is applicable to the assay method of the present invention, the detection method of the present invention, and the assay kit of the present invention. Thus, the solid phase of the invention is remarkably useful.

Through the assay method 1 or 2 of the present invention, $\beta_2$-GPI, an autoantibody against a complex of $\beta_2$-GPI and the derivative of the present invention, or a similar substance can be assayed quickly in a simple manner. Thus, the assay methods 1 and 2 of the present invention are remarkably useful.

Through the detection method of the present invention, a disease can be detected quickly in a simple manner. Thus, the detection method of the present invention is remarkably useful.

By use of the assay kit 1 or 2 of the present invention, the assay method 1 or 2 can be carried out more quickly and in a simpler manner. Thus, the assay kits of the present invention are remarkably useful.

The invention claimed is:

1. A cholesterol derivative represented by the following formula (3).

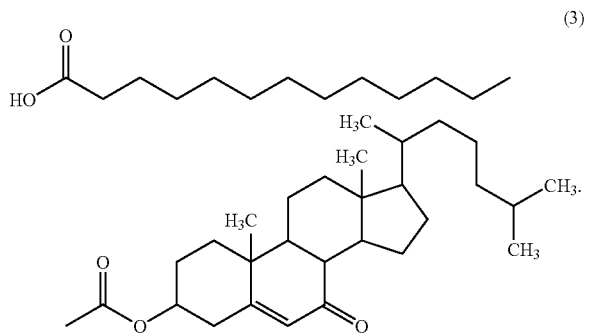
(3)

2. A cholesterol derivative represented by the following formula (4).

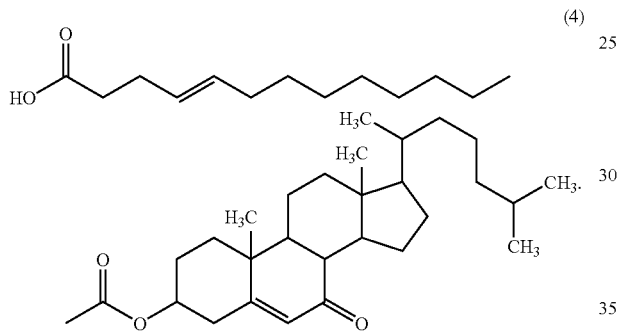
(4)

3. A cholesterol derivative represented by the following formula (7).

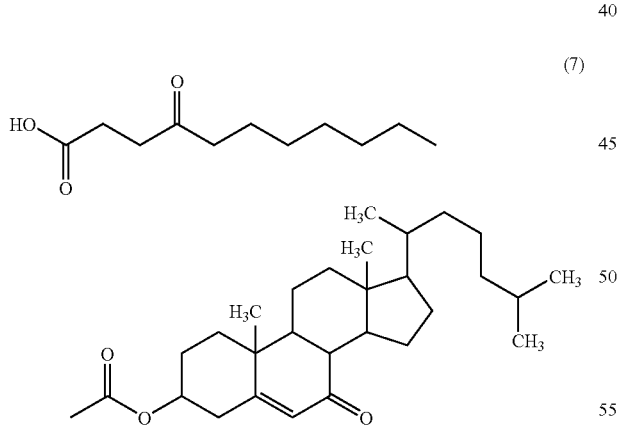
(7)

4. An assay method for $\beta_2$-GPI, characterized in that the method includes at least the following steps:

a step of forming a complex of $\beta_2$-GPI and a cholesterol derivative immobilized on a solid phase by bringing a specimen into contact with the solid phase (Step 1), wherein the cholesterol derivative is represented by the following formula (3), (4) or (7):

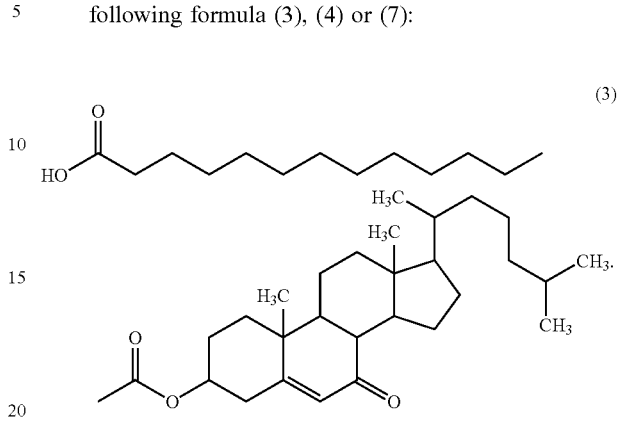
(3)

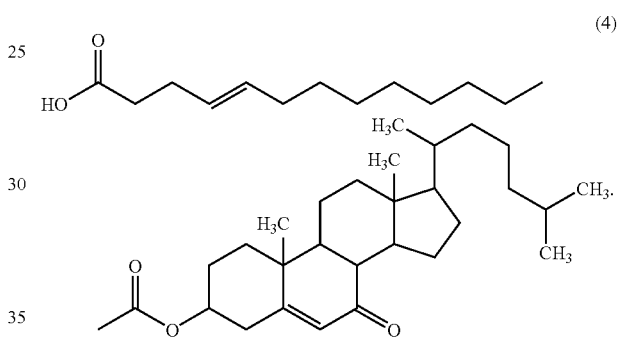
(4)

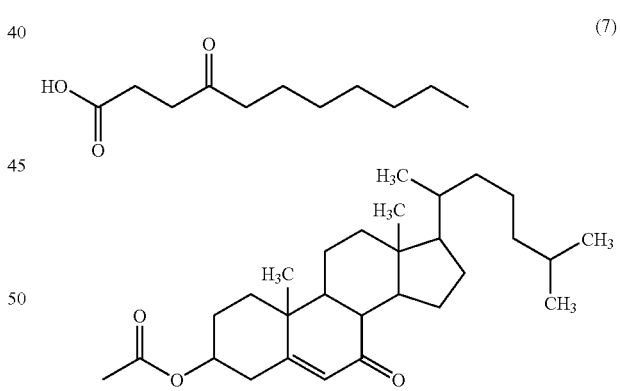
(7)

and a step of detecting $\beta_2$-GPI contained in the complex which has been formed in Step 1 (Step 2).

* * * * *